US012774339B2

(12) United States Patent
Deschamps et al.

(10) Patent No.: US 12,774,339 B2
(45) **Date of Patent: *Oct. 27, 2026**

(54) CAR-T CELLS TARGETING IL-1RAP AND THEIR USE IN ACUTE MYELOID LEUKEMIA (AML)

(71) Applicants: ETABLISSEMENT FRANCAIS DU SANG, La Plaine Saint-Denis (FR); INSTITUT NATIONAL DE LA SANTE ET DE LA RECHERCHE MEDICALE (INSERM), Paris (FR); CENTRE HOSPITALIER UNIVERSITAIRE DE BESANCON, Besancon (FR); UNIVERSITE DE FRANCHE—COMTE, Besancon (FR)

(72) Inventors: Marina Deschamps, Antorpe (FR); Christophe Ferrand, Dampierre (FR); Fabrice Larosa, Velars sur Ouche (FR); Walid Warda, Besancon (FR)

(73) Assignees: ETABLISSEMENT FRANCAIS DU SANG, La Plaine Saint-Denis Cedex (FR); INSTITUT NATIONAL DE LA SANTA ET DE LA RECHERCHE MEDICALE (INSERM), Paris (FR); CENTRE HOSPITALIER UNIVERSITAIRE DE BESANCON, Besancon (FR); UNIVERSITE DE FRANCHE-COMTE, Besancon (FR)

( * ) Notice: Subject to any disclaimer, the term of this patent is extended or adjusted under 35 U.S.C. 154(b) by 1336 days.

This patent is subject to a terminal disclaimer.

(21) Appl. No.: 17/613,594

(22) PCT Filed: May 27, 2020

(86) PCT No.: PCT/EP2020/064636

§ 371 (c)(1),
(2) Date: Nov. 23, 2021

(87) PCT Pub. No.: WO2020/239801

PCT Pub. Date: Dec. 3, 2020

(65) Prior Publication Data

US 2022/0235138 A1 Jul. 28, 2022

(30) Foreign Application Priority Data

May 28, 2019 (EP) .................................... 19305678

(51) Int. Cl.

| | |
|---|---|
| ***A61K 40/31*** | (2025.01) |
| ***A61K 40/11*** | (2025.01) |
| ***A61K 40/42*** | (2025.01) |
| ***A61P 35/02*** | (2006.01) |
| ***C07K 14/705*** | (2006.01) |
| ***C07K 16/28*** | (2006.01) |
| ***C12N 5/0783*** | (2010.01) |
| *A61K 38/00* | (2006.01) |
| *A61K 39/00* | (2006.01) |

(52) U.S. Cl.

CPC .......... *C07K 16/2866* (2013.01); *A61K 40/11* (2025.01); *A61K 40/31* (2025.01); *A61K 40/4217* (2025.01); *A61P 35/02* (2018.01); *C07K 14/7051* (2013.01); *C07K 14/70521* (2013.01); *C07K 14/70578* (2013.01); *C12N 5/0636* (2013.01); *A61K 38/00* (2013.01); *A61K 2039/505* (2013.01); *A61K 2239/31* (2023.05); *A61K 2239/38* (2023.05); *A61K 2239/48* (2023.05); *C07K 2317/53* (2013.01); *C07K 2317/565* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search

None

See application file for complete search history.

(56) References Cited

U.S. PATENT DOCUMENTS 11,839,630 B2 12/2023 Ferrand et al.

FOREIGN PATENT DOCUMENTS

| | | | |
|---|---|---|---|
| CN | 106831998 | A | 6/2017 |
| CN | 111712517 | A | 9/2020 |
| JP | 2019505552 | A | 2/2019 |
| JP | 2021503952 | A | 2/2021 |
| JP | 7307083 | B2 | 7/2023 |

OTHER PUBLICATIONS

Askmyr, Blood, May 2, 2013 x vol. 121, No. 18 (Year: 2013).*
Bone Marrow Transplantation (2017) 52, 317 (Year: 2017).*
International Search Report and Written Opinion issued in corresponding International Application No. PCT/EP2020/064636 on Aug. 21, 2020, 11 pages.
Walid, W. et al., "CML Hematopoietic Stem Cells Expressing IL1RAP Can Be Targeted by Chimeric Antigen Receptor-Engineered T Cells", Cancer Research, Dec. 4, 2018, vol. 79, No. 3, pp. 663-675.
European Search Report issued in corresponding International Application No. EP19305678 on Nov. 13, 2019, 3 pages.
Askmyr, M., et al., "Selective killing of candidate AML stem cells by antibody targeting of IL1RAP," Blood 121(18):3709-3713, American Society of Hematology, United States (May 2013).

(Continued)

*Primary Examiner* — Michael Allen
*Assistant Examiner* — Imma Barrera
(74) *Attorney, Agent, or Firm* — STERNE, KESSLER, GOLDSTEIN & FOX P.L.L.C.

(57) ABSTRACT

The present invention is relative to a cell comprising a nucleic acid molecule encoding a chimeric antigen receptor (CAR) for use in the treatment of acute myeloid leukemia (AML), wherein the CAR comprises an antibody or antibody fragment which includes an anti-IL-1RAP binding domain, a transmembrane domain, and an intracellular signaling domain comprising at least a stimulatory domain

16 Claims, 31 Drawing Sheets

Specification includes a Sequence Listing.

(56) References Cited

OTHER PUBLICATIONS

Barreyro, L., et al., "Overexpression of IL-1 receptor accessory protein in stem and progenitor cells and outcome correlation in AML and MDS", Blood, 120(6):1290-1298, American Society of Hematology, United States (Aug. 2012).

Ågerstam, H., et al., "Antibodies targeting human IL1RAP (ILIR3) show therapeutic effects in xenograft models of acute myeloid leukemia", PNAS, 112(34):10786-10791, National Academy of Sciences, United States (Aug. 2015).

* cited by examiner

FIGURE 14B (CONTINUATION)
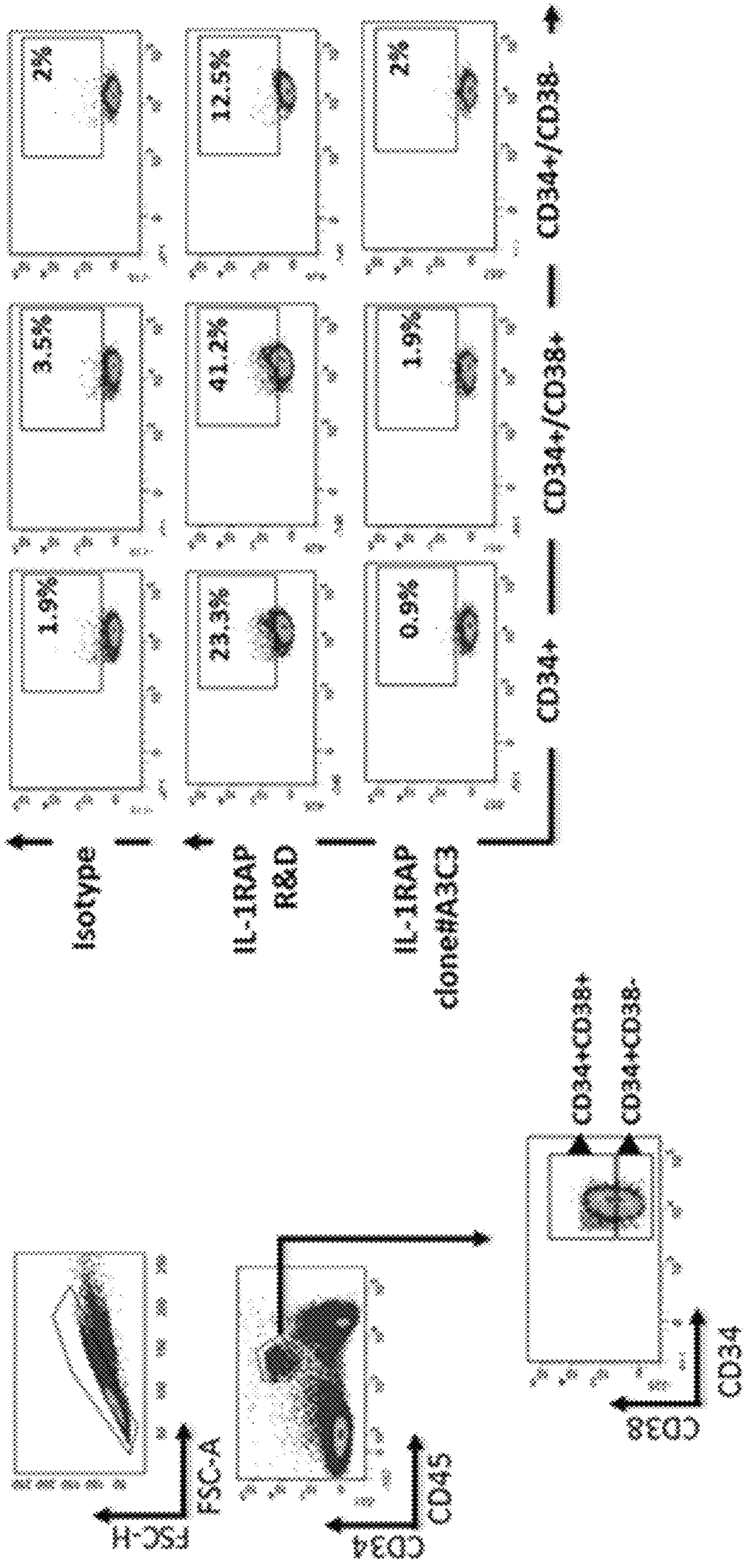

** : p<0,01

CAR-T CELLS TARGETING IL-1RAP AND THEIR USE IN ACUTE MYELOID LEUKEMIA (AML)

CROSS REFERENCE TO RELATED APPLICATIONS

This application is the National Phase of PCT International Application No. PCT/EP2020/064636, filed on May 27, 2020, which claims priority to European Patent Application No. 19305678.5, filed on May 28, 2019, the entire disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on 23 Nov. 2021, is named 0177_0186_ST25.txt and is 9,662 bytes in size.

BACKGROUND OF THE INVENTION

The present invention is relative to a cell comprising a nucleic acid molecule encoding a chimeric antigen receptor (CAR), for use in the treatment of acute myeloid leukemia (AML), wherein the CAR comprises an antibody or antibody fragment which includes an anti-IL-1RAP binding domain, a transmembrane domain, and an intracellular signaling domain comprising at least a stimulatory domain.

Acute myeloid leukemia (AML; also known as “acute myeloid leukemia”, “acute myelocytic leukemia”, “acute myeloblastic leukemia”, “acute granulocytic leukemia”, and “acute nonlymphocytic leukemia”) is a devastating clonal hematopoietic stem cell neoplasm characterized by uncontrolled proliferation and accumulation of leukemic blasts in the bone marrow, peripheral blood, and occasionally in other tissues. These cells disrupt normal hematopoiesis and rapidly cause bone marrow failure and death. AML is the most common type of acute leukemia in adults and accounts for the largest number of annual deaths from leukemia. AML progresses rapidly and is typically fatal within weeks or months if left untreated. There were approximately 20,830 new cases of AML in the United States in 2015, and 10,460 patients died of the disease. The median age at diagnosis is approximately 70 years. Overall 5-year survival in patients under 60 years is only about 30-40% and less than 10% for patients 60 years of age or older.

The present standard of care for AML consists of remission induction treatment by high dose of chemotherapy or radiation, followed by consolidation, comprised of allogeneic stem cell transplantation and additional courses of chemotherapy as needed. Most patients treated this way will achieve a complete, but transient, remission. Once relapsed, the disease is increasingly resistant to further therapy.

While outcomes for younger patients have improved somewhat during the last three decades, the dismal outcomes for older patients have remained essentially unchanged. Unfortunately, the majority of patients with AML experience disease relapse, including those who achieve initial complete remission. Allogeneic hematopoietic stem cell transplantation in second remission offers the only chance for long-term survival, but this option is not available to most relapsed AML patients, because either they do not achieve second remission, or they cannot tolerate the procedure.

There are multiple multi-agent chemotherapy salvage regimens for relapsed AML (such as MEC (mitoxantrone, etoposide, and cytarabine) and FLAG-IDA (fludarabine, cytarabine, idarubicin, granulocyte colony-stimulating factor)). However, there is no accepted standard of care because none of these regimens is superior to the others and none results in long-term survival. Clinical trials are recommended in the NCCN (National Comprehensive Cancer Network) and other guidelines, and relapsed AML is widely recognized as an urgent unmet medical need.

A number of novel approaches to treat AML, in particular relapsed AML, including antibody-drug bispecific T-cell-engaging antibody (AMG330) and CAR-T cells (CART-33 cells or CART-123 cells) are currently being investigated. However, several of the novel approaches have been held back due to clinical toxicity and/or lack of efficacy. There is therefore a clear need for new efficient therapies with acceptable toxicity profiles.

In AML, gene expression profiling, cell surface staining, western blotting studies have revealed a cell surface biomarker (IL-1RAP, IL-1R3, C3orf13 or IL-1RAcP) that is expressed by the leukemic, but not the normal $CD34^+$/$CD38^-$ hematopoietic stem cells. Moreover, IL-1RAP expression is correlated with the tumor burden as well as clinical phase of the AML disease.

SUMMARY OF THE INVENTION

IL-1RAP (interleukin-1 receptor accessory protein, Genbank accession no AAB4059) is a co-receptor of the IL-1 and IL33 receptor, involved in IL-1 signaling, that activates different signaling pathways, including MAP Kinase, p38, NF-κB and others genes implied in inflammation and proliferation. This protein is expressed at the tumor cell surface. IL-1RAP is a thus a promising tumor-associated antigen.

The applicant has discovered that, by using this CART-IL-1RAP cells, it is possible to can treat patient having AML.

The invention therefore relates to a cell expressing a nucleic acid molecule encoding a chimeric antigen receptor (CAR) at its membrane for use in the treatment of acute myeloid leukemia (AML), wherein the CAR comprises an antibody or antibody fragment which includes an anti-IL-1RAP binding domain, a transmembrane domain, and an intracellular signaling domain comprising at least a stimulatory domain, and wherein said anti-IL-1RAP binding domain comprises:

(i) a light chain comprising a complementary determining region 1 (CDR1) having at least 80% identity with the amino acid sequence SEQ ID NO: 6, a complementary determining region 2 (CDR2) having at least 80% identity with the amino acid sequence SEQ ID NO: 7 and a complementary determining region 3 (CDR3) having at least 80% identity with the amino acid sequence SEQ ID NO: 8, and (ii) a heavy chain comprising a complementary determining region 1 (CDR1) having at least 80% identity with the amino acid sequence SEQ ID NO: 12, a complementary determining region 2 (CDR2) having at least 80% identity with the amino acid sequence SEQ ID NO: 13 and a complementary determining region 3 (CDR3) having at least 80% identity with the amino acid sequence SEQ ID NO: 14.

T cells expressing a CAR are referred to herein as “CAR T cells” or “CAR modified T cells”. T cells expressing a CAR targeting IL1-RAP are referred to herein as “CART-IL1-RAP cells” or “CART-IL1-RAP modified T cells”.

The cells for use according to the present invention are genetically modified to express the CARs described herein, for use in the treatment of AML. As used herein, the term "genetically engineered" or "genetically modified" refers to the addition of extra genetic material in the form of DNA or RNA into the total genetic material in a cell.

DESCRIPTION OF THE FIGURES

FIG. 20: Efficacy of IL-1RAP CAR-T cells in a human AML mouse xenograft model. Immunodeficient NSG-S mice were irradiated (2.5 Gy) and on the following day (day-3) were injected with either $1\times10^6$ of HL-60 or Molm-13 or Mono-Mac-6 luciferase-expressing AML cells.

DETAILED DESCRIPTION OF THE INVENTION

Figure 1:
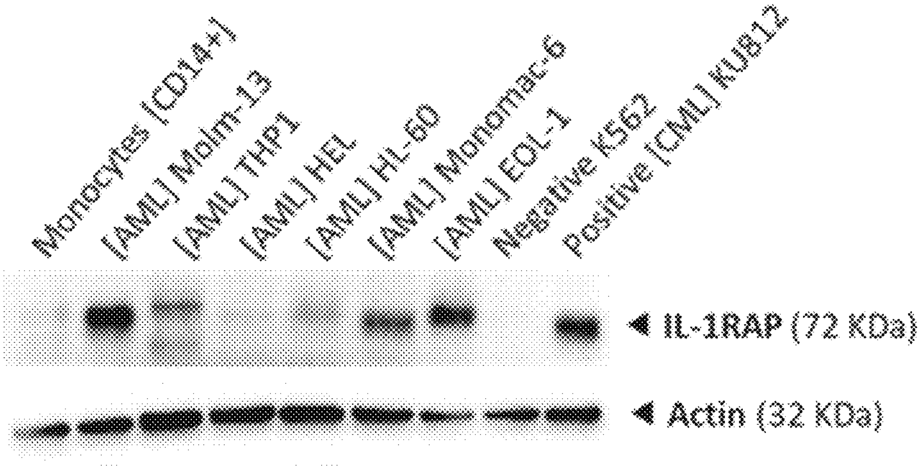
FIG. 1: Western blotting of different hematopoietic AML cell lines and CD14+ cell sorted monocytes.

The invention therefore relates to a cell comprising a nucleic acid molecule encoding a chimeric antigen receptor (CAR) for use in the treatment of acute myeloid leukemia (AML), wherein the CAR comprises an antibody or antibody fragment which includes an anti-IL-1RAP binding domain, a transmembrane domain, and an intracellular signaling domain comprising at least a stimulatory domain, and wherein said anti-IL-1RAP binding domain comprises:

(i) a light chain comprising a complementary determining region 1 (CDR1) having at least 80%, 85%, 90%, 95%, 96%, 97%, 98%, 99%, or 100% identity with the amino acid sequence SEQ ID NO: 6, a complementary determining region 2 (CDR2) having at least 80%, 85%, 90%, 95%, 96%, 97%, 98%, 99%, or 100% identity with the amino acid sequence SEQ ID NO: 7 and a complementary determining region 3 (CDR3) having at least 80%, 85%, 90%, 95%, 96%, 97%, 98%, 99%, or 100% identity with the amino acid sequence SEQ ID NO: 8, and (ii) a heavy chain comprising a complementary determining region 1 (CDR1) having at least 80%, 85%, 90%, 95%, 96%, 97%, 98%, 99%, or 100% identity with the amino acid sequence SEQ ID NO: 12, a complementary determining region 2 (CDR2) having at least 80%, 85%, 90%, 95%, 96%, 97%, 98%, 99%, or 100% identity with the amino acid sequence SEQ ID NO: 13 and a complementary determining region 3 (CDR3) having at least 80%, 85%, 90%, 95%, 96%, 97%, 98%, 99%, or 100% identity with the amino acid sequence SEQ ID NO: 14.

The following Table summarizes the sequence identifiers

TABLE 1 sequence listing

| SEQ ID | Name | Sequence |
|---|---|---|
| SEQ ID NO: 1 | Nucleotide sequence coding chain H (VH) of murine scFv anti-IL-1RAP (with leader sequence in grey) | atgggatggagctgtatcatcctcttcttggtagcaa<br>cagctacaggtgtcaactcccaggtccaactgcag<br>cagcctggggctgagcttatgatgcctggggcttca<br>gtgaaagtgtcctgcgaggcttctggctacacattc<br>actgactcctggatgcactgggtgaagcagaggcc<br>tggacaaggccttgagtggatcggagcgattgatc<br>cttctgatagttatactacctataatcaaaaattcac<br>gggcaaggccacattgagtgtagacgaatcctcca<br>acacagcctacatgcagctcagcagcctgacatct<br>gaggactctgcggtctattactgtgcaaggtattact<br>ccggtagtaactacatatcgccctttccttactgggg<br>ccaagggactctggtcactgtctctgca |

TABLE 1-continued

| sequence listing | | |
|---|---|---|
| SEQ ID | Name | Sequence |
| SEQ ID No 2 | Amino acid sequence of chain H (VH) of murine scFv anti-IL-1RAP (with leader sequence in grey) | MGWSCIILFLVATATGVNSQVQLQQPGAE LMMPGASVKVSCEASGYTFTDSWMHWVK QRPGQGLEWIGAIDPSDSYTTYNQKFTGK ATLSVDESSNTAYMQLSSLTSEDSAVYYC ARYYSGSNYISPFPYWGQGTLVTVSA |
| SEQ ID No 3 | Nucleotide sequence coding chain K (VL) of murine scFv anti-IL-1 RAP | atggagtcacagattcaggtctttgtattcgtgtttct ctggttgtctggtgttgacggagacattgtgatgac ccagtctcacaaattcatgtccacatcagtaggaga cagggtcaccatcacctgcaaggccagtctggatg tgagtactgctgtggcctggtatcaacagaaacca ggacaatctcctaaactactgatttactcggcatcct accggtacactggagtccctgatcgcttcactggca gtggatctgggacggatttcactttcaccatcagca gtgtgcaggctgaagacctggcagtttattactgtc agcaacattatagtcctccattcacgttcggctcgg ggacaaacttggagataaaac |
| SEQ ID No 4 | Amino acid sequence of chain K (VL) of murine scFv anti-IL-1RAP | MESQIQVFVFVFLWLSGVDGDIVMTQSHK FMSTSVGDRVTITCKASLDVSTAVAWYQQ KPGQSPKLLIYSASYRYTGVPDRFTGSGSG TDFTFTISSVQAEDLAVYYCQQHYSPPFTF GSGTNLEIK |
| SEQ ID No 5 | Linker between the VH and VL domains (aa) | GGSGGGGSGGGGSVD |
| SEQ ID No 6 | CDR1 of the light chain (aa) | LDVSTA |
| SEQ ID NO: 7 | CDR2 of the light chain (aa) | SAS |
| SEQ ID NO: 8 | CDR3 of the light chain (aa) | QQHYSPPFT |
| SEQ ID NO: 9 | CDR1 of the light chain (nucleotides) | ctggatgtgagtactgct |
| SEQ ID NO: 10 | CDR2 of the light chain (nucleotides) | tcggcatcc |
| SEQ ID NO: 11 | CDR3 of the light chain (nucleotides) | cagcaacattatagtcctccattcacg |
| SEQ ID NO: 12 | CDR1 of the heavy chain (aa) | GYTFTDSW |
| SEQ ID NO: 13 | CDR2 of the heavy chain (aa) | IDPSDSYT |
| SEQ ID NO: 14 | CDR3 of the heavy chain (aa) | ARYYSGSNYISPFPY |
| SEQ ID NO: 15 | CDR1 of the heavy chain (nucleotides) | ggctacacattcactgactcctgg |
| SEQ ID NO: 16 | CDR2 of the heavy chain (nucleotides) | attgatccttctgatagttatact |
| SEQ ID NO: 17 | CDR3 of the heavy chain (nucleotides) | gcaaggtattactccggtagtaactacatatcgccctttccttac |
| SEQ ID NO: 18 | Amino acid sequence of murine scFv anti-IL-1 RAP (i.e. #A3C3) | MGWSCIILFLVATATGVNSQVQLQQPGAE LMMPGASVKVSCEASGYTFTDSWMHWVK QRPGQGLEWIGAIDPSDSYTTYNQKFTGK ATLSVDESSNTAYMQLSSLTSEDSAVYYC ARYYSGSNYISPFPYWGQGTLVTVSA GGSGGGGSGGGGSVDMESQIQVFVFVFL WLSGVDGDIVMTQSHKFMSTSVGDRVTI TCKASLDVSTAVAWYQQKPGQSPKLLIYS |

TABLE 1-continued

| sequence listing | | |
|---|---|---|
| SEQ ID | Name | Sequence |
| | | ASYRYTGVPDRFTGSGSGTDFTFTISSVQ AEDLAVYYCQQHYSPPFTFGSGTNLEIK |

The terms "#E3C3" and "#A3C3" are understood to be identical: #E3C3 being able to be freely used to refer to #A3C3 and vice versa.

The sequences of the hinge region of IgG1, IgG4, CD8alpha, 4-11B, CD3 zeta, CD28 and ICasp9 genes can be found on Genbank.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., Molecular Cloning: A Laboratory Manual (3rd Edition, 2001); Sambrook, et al., Molecular Cloning: A Laboratory Manual (2nd Edition, 1989); Maniatis et al., Molecular Cloning: A Laboratory Manual (1982); Ausubel et al., Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998) Current Protocols in Immunology Q. E. Coligan, A. M. Kruisbeek, D. H. Margulies, E. M. Shevach and W. Strober, eds., 1991); Annual Review of Immunology; as well as monographs in journals such as Advances in Immunology.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein.

As would be understood by the skilled person and as described elsewhere herein, a complete antibody comprises two heavy chains and two light chains. Each heavy chain consists of a variable region and a first, second, and third constant regions, while each light chain consists of a variable region and a constant region. Mammalian heavy chains are classified as α, δ, ε, γ, and μ, and mammalian light chains are classified as λ or κ. Immunoglobulins comprising the α, δ, ε, γ, and μ heavy chains are classified as immunoglobulin (Ig)A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

Light and heavy chain variable regions contain a "framework" region interrupted by three hypervariable regions, also called "complementarity-determining regions" or "CDRs." The CDRs can be defined or identified by conventional methods, such as by sequence according to Kabat et al (Wu, TT and Kabat, E. A., J Exp Med. 132(2):211-50, (1970); Borden, P. and Kabat E. A., PNAS, 84: 2440-2443 (1987); (see, Kabat et al., Sequences of Proteins of Immunological Interest, U.S. Department of Health and Human Services, 1991), or by structure according to Chothia et al (Choithia, C. and Lesk, A. M., J Mol. Biol., 196(4): 901-917 (1987), Choithia, C. et al, Nature, 342: 877-883 (1989)).

The sequences of the framework regions of different light or heavy chains are relatively conserved within a species, such as humans. The framework region of an antibody, that is the combined framework region of the constituent light and heavy chains, serves to position and align the CDRs in three-dimensional space. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, the CDRs located in the variable domain of the heavy chain of the antibody are referred to as CDRH1, CDRH2, and CDRH3, whereas the CDRs located in the variable domain of the light chain of the antibody are referred to as CDRL1, CDRL2, and CDRL3. Antibodies with different specificities (i.e., different combining sites for different antigens) have different CDRs.

References to "VH" or "$V_H$" refer to the variable region of an immunoglobulin heavy chain, including that of an antibody, Fv, scFv, Fab, or other antibody fragment as disclosed herein.

References to "VL" or "$V_L$" refer to the variable region of an immunoglobulin light chain, including that of an antibody, Fv, scFv, dsFv, Fab, or other antibody fragment as disclosed herein.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include chimeric monoclonal antibodies and humanized monoclonal antibodies.

The articles "a," "an," and "the" are used herein to refer to one or to more than one (i.e., to at least one) of the grammatical object of the article.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Reference throughout this specification to "one embodiment" "an embodiment" "a particular embodiment", a certain embodiment" "an additional embodiment" or "a further embodiment" or combinations thereof means that a particular feature, structure or characteristic described in connection with the embodiment is included in at least one embodiment of the present invention.

For the purposes of the present invention, the "identity" or "homology" is calculated by comparing two aligned sequences in a comparison window. The alignment of the sequences makes it possible to determine the number of positions (nucleotides or amino acids) common to the two sequences in the comparison window. The number of common positions is then divided by the total number of positions in the comparison window and multiplied by 100 to obtain the percentage of homology. The determination of the percentage of sequence identity can be done manually or by using well-known computer programs.

The present invention provides immune effector cells genetically engineered with vectors designed to express genetically engineered receptors that redirect cytotoxicity toward tumor cells for use in the treatment of acute myeloid leukemia (AML). These genetically engineered receptors referred to herein as chimeric antigen receptors (CARs).

CARs are molecules that combine antibody-based specificity for a target antigen (e.g. tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

As used herein, the terms, "binding domain," "extracellular binding domain," "antigen-specific binding domain," and "extracellular antigen specific binding domain," are used interchangeably and provide a CAR with the ability to specifically bind to the target antigen of interest. A binding domain may comprise any protein, polypeptide, oligopeptide, or peptide that possesses the ability to specifically recognize and bind to a biological molecule {e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest. The terms "specific binding affinity" or "specifically binds" or "specifically bound" or "specific binding" or "specifically targets" as used herein, describe binding of one molecule to another at greater binding affinity than background binding. A binding domain (or a CAR comprising a binding domain or a fusion protein containing a binding domain) "specifically binds" to a target molecule if it binds to or associates with a target molecule with an affinity or Ka (i.e., an equilibrium association constant of a particular binding interaction with units of 1/M) of, for example, greater than or equal to about $10^5 M^{-1}$. Affinities of binding domain polypeptides and CAR proteins according to the present disclosure can be readily determined using conventional techniques like competitive ELISA (enzyme-linked immunosorbent assay).

The antibody is a human antibody, a murine antibody, a chimeric antibody, or a humanized antibody.

In certain preferred embodiments, the antibody is a chimeric antibody (such as a chimeric monoclonal antibody) that specifically binds to a surface protein on a tumor cell. A "chimeric" antibody is an immunoglobulin including a human framework region and one or more CDRs from a non-human (for example a mouse, rat, or synthetic) immunoglobulin. Hence, all parts of a chimeric immunoglobulin, except possibly the CDRs, are substantially identical to corresponding parts of natural human immunoglobulin sequences. Chimeric or other monoclonal antibodies can have additional conservative amino acid substitutions, which have substantially no effect on antigen binding or other immunoglobulin functions. Chimeric antibodies can be constructed by means of genetic engineering (see for example, U.S. Pat. No. 5,585,089).

Antibodies include antigen binding fragments thereof, such as Fab fragments, Fab' fragments, F(ab)'2 fragments, F(ab)'3 fragments, Fv, single chain Fv proteins ("scFv") and portions of full length antibodies responsible for antigen binding. The term also includes genetically engineered forms such as humanized antibodies, heteroconjugate antibodies (such as, bispecific antibodies) and antigen binding fragments thereof.

"Single-chain Fv" or "scFv" antibody fragments comprise the VH and VL domains of antibody, wherein these domains are present in a single polypeptide chain and in either orientation (e.g., VL-VH or VH-VL).

Single chain antibodies may be cloned form the V region genes of a hybridoma specific for a desired target. The production of such hybridomas has become routine. A technique which can be used for cloning the variable region heavy chain (VH) and variable region light chain (VL) has been described, for example, in Orlandi et al, PNAS, 1989; 86: 3833-3837.

Generally, the scFv polypeptide further comprises a polypeptide linker between the VH and VL domains which enables the scFv to form the desired structure for antigen binding.

CARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G)n; glycine-serine polymers (Gi_sSi_5)n, where n is an integer of at least one, two, three, four, or five; glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses significantly more phi-psi space than even alanine, and is much less restricted than residues with longer side chains {see Scheraga, Rev. Computational Chem. 1 1173-142 (1992)). The ordinarily skilled artisan will recognize that design of a CAR in particular embodiments can include linkers that are all or partially flexible, such that the linker can include a flexible linker as well as one or more portions that confer less flexible structure to provide for a desired CAR structure.

In a particular embodiment, the linker is between the VH and VL domains.

In a particular embodiment, the linker comprises or consists in the amino acid sequence of SEQ ID NO°5.

In one embodiment, the IL-1RAP binding domain is a scFv comprising a light chain variable region comprising an amino acid sequence having at least one, two or three modifications but not more than 30, 20 or 10 modifications of an amino acid sequence of a light chain variable regions of SEQ ID NO: 4 and a heavy chain variable region comprising an amino acid sequence having at least one, two or three modifications but not more than 30, 20 or 10 modifications of an amino acid sequence of a heavy chain variable region of SEQ ID NO: 2.

Preferably, the IL-1RAP binding domain is a scFv comprising (i) a light chain variable region comprising a complementary determining region 1 (CDR1) having at least 80%, 85%, 90%, 95%, 96%, 97%, 98%, 99% or having 100% identity with the amino acid sequence SEQ ID NO: 6, a complementary determining region 2 (CDR2) having at least 80%, 85%, 90%, 95%, 96%, 97%, 98%, 99% or having 100% identity with the amino acid sequence SEQ ID NO: 7 and a complementary determining region 3 (CDR3) having at least 80%, 85%, 90%, 95%, 96%, 97%, 98%, 99% or having 100% identity with the amino acid sequence SEQ ID NO: 8, and (ii) a heavy chain variable region comprising a complementary determining region 1 (CDR1) having at least 80%, 85%, 90%, 95%, 96%, 97%, 98%, 99% or having 100% identity with the amino acid sequence SEQ ID NO: 12, a complementary determining region 2 (CDR2) having at least 80%, 85%, 90%, 95%, 96%, 97%, 98%, 99% or having 100% identity with the amino acid sequence SEQ ID NO: 13 and a complementary determining region 3 (CDR3) having at least 80%, 85%, 90%, 95%, 96%, 97%, 98%, 99% or having 100% identity with the amino acid sequence SEQ ID NO: 14.

The binding domain of the CAR is generally followed by one or more "hinge regions", which play a role in positioning the antigen binding domain away from the effector cell surface to enable proper cell/cell contact, antigen binding and activation. A CAR generally comprises one or more hinge regions between the binding domain and the transmembrane domain. The hinge region may be derived either from a natural, synthetic, semi-synthetic, or recombinant source.

Preferably, the anti-IL-1RAP binding domain is connected to the transmembrane domain by a hinge region.

In an embodiment, the hinge region comprises the hinge sequence of IgG1 or a sequence with 95-99% identity thereof. IgG hinges are encoded by single exons. Thus, the term "hinge sequence of IgG1" as used herein has the same meaning as commonly understood by those of ordinary skill in the art to which the invention belongs, i.e. the 15 amino acid residues encoded by the IgG1 exon for the hinge (Fundamental Immunology, Fifth edition, Chapter 3, Immunoglobulins: Structure and Function—The immunoglobulin Hinge).

In further embodiments, the hinge region comprises the hinge sequence of IgG4 or a sequence with 95-99% identity thereof. In further embodiments, the hinge region may also comprise the CH2-CH3 region of IgG1 or IgG4 or a sequence with 95-99% identity thereof.

In further embodiments, the hinge region comprises CD8alpha or a sequence with 95-99% identity thereof.

The "transmembrane domain" is the portion of the CAR that fuses the extracellular binding portion and intracellular signaling domain and anchors the CAR to the plasma membrane of the immune effector cell. The transmembrane domain may be derived either from a natural, synthetic, semi-synthetic, or recombinant source.

Preferably, the encoded CAR includes a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD 154, more preferably CD28.

In particular embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term "intracellular signaling domain" is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g. a TCR/CD3 complex) and co-stimulatory signaling domains that act in an antigen-independent manner to provide a secondary or co-stimulatory signal. In preferred embodiments, a CAR contemplated herein comprises an intracellular signaling domain that comprises one or more "co-stimulatory signaling domain"."

In an embodiment, the isolated nucleic acid molecule may encode an intracellular signaling domain comprising at least one costimulatory domain. In this embodiment, the intracellular signaling domain therefore comprises at least one costimulatory domain.

As used herein, the term "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen.

Preferably, the at least one costimulatory domain of the functional intracellular signaling domain is obtained from one or more protein selected from the group consisting of OX40, CD2, CD27, CD28, CDS, CD3 zeta, ICAM-1, LFA-1 (CD11a/CD18), ICOS (CD278), and 4-1BB (CD137).

More preferably, the costimulatory domain obtained from 4-1BB (CD137) has a sequence having 95-99% identity with the amino acid sequence of the costimulatory domain of 4-1BB.

More preferably, the costimulatory domain obtained from CD3 zeta has a sequence having 95-99% identity with the amino acid sequence of the costimulatory domain of CD3 zeta.

In another embodiment, the intracellular signaling domain comprises a costimulatory domain obtained from 4-1BB and/or a costimulatory domain obtained from CD3 zeta.

In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

The cell that can be used according to the invention may be isolated. An "isolated cell" refers to a cell that has been obtained from an in vivo tissue or organ and is substantially free of extracellular matrix.

The cell that is used for treating AML according to the invention may be prepared by inserting; within the genome of a host cell, the nucleic acid molecule encoding the chimeric antigen receptor (CAR) using a vector.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA.

The cell that is used for treating AML according to the invention may be prepared using a vector comprising a nucleic acid molecule encoding the CAR, said vector is selected from a DNA, a RNA, a plasmid, a lentivirus vector, an adenoviral vector, or a retrovirus vector, preferably a lentivirus vector.

In some embodiments, the vector comprises a promoter, preferably an EF-1 alpha promoter.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Thus, the T cells transduced with the vector can elicit a stable, long-term, and persistent CAR-mediated T-cell response.

In particular embodiments, the T cell is transduced with a retroviral vector, e.g., a lentiviral vector, encoding the CAR.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

The term "lentiviral vector" refers to a viral vector or plasmid containing structural and functional genetic elements, or portions thereof, including LTRs that are primarily derived from a lentivirus.

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication.

In one embodiment, SIN vector backbones are preferred.

Preferably, the vector used further comprises a promoter, e.g. an EF-1 alpha promoter.

The term "promoter" as used herein refers to a recognition site of a polynucleotide (DNA or RNA) to which an R A polymerase binds. An R A polymerase initiates and transcribes polynucleotides operably linked to the promoter. In a particular embodiment, it may be desirable to express a polynucleotide comprising a CAR from a promoter that provides stable and long-term CAR expression in T cells and at sufficient levels to redirect the T cells to cells expressing the target antigen.

The cell for use according to the invention is preferably a T cell, e.g. human T cell, more preferably a CD8+ T cell, e.g. human CD8+ T cell. In a preferred embodiment, the cell for use according to the invention (e.g. T cell) expresses the CAR at its membrane. The term "at its membrane" as used herein has the same meaning as commonly understood by those of ordinary skill in the art to which the invention belongs, i.e. "at the cell surface membrane".

In particular embodiments, prior to in vitro manipulation or genetic modification of the immune effector cells described herein, the source of cells is obtained from a subject. In particular embodiments, the cells for use according to the invention encompass T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation. Cells from the circulating blood of an individual may be obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing.

T cells may be isolated from peripheral blood mononuclear cells by lysing the red blood cells and depleting the monocytes, for example, by centrifugation through a PERCOLL™ gradient. A specific subpopulation of T cells, expressing one or several markers like CD4 or CD8 can be further isolated by positive or negative selection techniques. For example, enrichment of a T cell population by negative selection can be accomplished with a combination of antibodies directed to surface markers unique to the negatively selected cells.

In some embodiments of the invention, the cell harboring the nucleic acid molecule encoding a chimeric antigen receptor (CAR) utilizes a suicide gene, including an inducible suicide gene to reduce the risk of direct toxicity (i.e. Graft versus host Diseases in allogeneic administration settings) and/or uncontrolled proliferation of gene modified cells. In specific aspects, the suicide gene is not immunogenic to the host harboring the polynucleotide or cell. A certain example of a suicide gene that may be used is inducible caspase-9 (iCASP9), thymidine kinase of Herpes simplex (HSV-tk), CD20, truncated EGFR, caspase-8 or cytosine deaminase.

Caspase-9 can be activated using a specific chemical inducer of dimerization (CID). Others systems may be activated by metabolizing prodrugs (Ganciclovir), or by binding antibodies (Rituximab, Cituximab)

Disclosed herein is a type of cellular therapy where T cells are genetically modified ex-vivo to express a CAR and the CAR T cell is infused to a recipient in need thereof. The infused cell is able to kill tumor cells in the recipient, preferably a human. Unlike antibody therapies, CAR T cells are able to replicate in vivo resulting in long-term persistence that can lead to sustained tumor control.

Moreover, CARs allow for the redirection and activation of effector T cells towards any cell surface molecule upon binding by the antibody derived receptor, and are independent of MHC restriction.

The genetically-modified cells, e.g. T cells, for use according to the invention are constructed starting from the own cells of the patient (autologous), but they can also originate from other allogenic donors to provide allogenic genetically-modified cells in bone marrow or peripheral hematopoietic stem cell allograft context (Donor lymphocytes infusion). These cells expressing a CAR molecule are useful to treat AML in a mammal, preferably a human, this disease being associated with cell surface IL-1RAP expression.

Preferably, these cells, e.g. T cells, express a CAR molecule comprising an antigen binding domain that is an anti-IL-1RAP scFv comprising an anti-IL-1RAP binding domain, a transmembrane domain of the CD28 protein, a costimulatory 4-1BB signaling domain, and a CD3 zeta signaling domain, wherein said anti-IL-1RAP binding domain comprises:

(i) a light chain comprising a complementary determining region 1 (CDR1) having at least 80%, 85%, 90%, 95%, 96%, 97%, 98%, 99% or having 100% identity with the amino acid sequence SEQ ID NO: 6, a complementary determining region 2 (CDR2) having at least 80%, 85%, 90%, 95%, 96%, 97%, 98%, 99% or having 100% identity with the amino acid sequence SEQ ID NO: 7 and a complementary determining region 3 (CDR3) having at least 80%, 85%, 90%, 95%, 96%, 97%, 98%, 99% or having 100% identity with the amino acid sequence SEQ ID NO: 8, and (ii) a heavy chain comprising a complementary determining region 1 (CDR1) having at least 80%, 85%, 90%, 95%, 96%, 97%, 98%, 99% or having 100% identity with the amino acid sequence SEQ ID NO: 12, a complementary determining region 2 (CDR2) having at least 80%, 85%, 90%, 95%, 96%, 97%, 98%, 99% or having 100% identity with the amino acid sequence SEQ ID NO: 13 and a complementary determining region 3 (CDR3) having at least 80%, 85%, 90%, 95%, 96%, 97%, 98%, 99% or having 100% identity with the amino acid sequence SEQ ID NO: 14.

AML may be any AML according to the European Leukemia Net (ELN) prognosis Classification and/or any subtypes AML according to the French-American-British (FAB) classification (FAB) classification In one embodiment, AML is relapse/refractory AML.

In another embodiment, AML is relapse/refractory AML with complex cytogenetic abnormalities, i.e. cytogenetic abnormalities according to the WHO classifications and/or AML with TP53 mutations.

TP53 is a tumor suppressor protein encoded by the TP53 gene, located on the short arm of chromosome 17. TP53 plays a pivotal role in maintaining genomic stability in response to DNA damage; it activates DNA repair programs, and triggers cell-cycle arrest. TP53 is mutated in over half of human cancers. In AML, mutated TP53 is predominantly observed in therapy related AML and/or in patients with complex karyotype. Studies from mouse models of AML have shown that gain of function mutations in hot spot regions can promote a more aggressive AML. Previous studies have demonstrated that presence of TP53 mutations correlates with poor response to chemotherapy and poor survival in patients with or without complex karyotype. In multivariate analysis, the presence of TP53 mutations without aberrant cytogenetic abnormality predicted for poor overall survival and inferior response to treatment. In some embodiments the AML is AML associated with IL-1RAP expression (also known as "IL1-RAP expressing AML" or "IL1-RAP+ AML").

In some embodiments, the AML associated with IL-1RAP expression is (i) relapsed/refractory forms of IL1-RAP+ AML or (ii) IL1-RAP+ AML with complex cytogenetic abnormalities and/or IL1-RAP+ AML with TP53 mutations.

The cell for use according to the invention may be used for treating patients of all ages, in particular patients having less than 60 years old, such as less than 20 years old (i.e. pediatric AML), and/or patients having 60 years old or more.

The cell, e.g. T cell, expressing the CAR molecule specific of IL-1RAP may be used in a method to treat AML in a human, wherein the human has already been treated by at least one therapy line, such as chemotherapy, immunotherapy or targeted therapy. Chemotherapy agents may be CPX-351, immunotherapy may be monoclonal antibodies, such as Antibody Drug Conjugates (ADC) (e.g. anti-CD33 linked to a toxin (Gemtuzumab ozogamicin)), bispecific antibodies (Bites, such as anti-CD33/CD3, anti-CD123/CD3 or others AML anti-cell surface markers/CD3). Targeted therapy agents may be an anti-mutated FLT3, such as Midostaurin or Quazartinib or agents targeting mutated IDH1/IDH2, such as IDH1 inhibitor (ivosidenib) or IDH2 inhibitor (enasidenib).

Preferably, the cell, e.g. T cell, expressing the CAR molecule specific of IL-1RAP is therefore useful in a method to treat AML in a mammal in association with at least one monoclonal antibody, such as anti-checkpoint inhibitors (i.e Anti PD-1, anti-PDL-1 or anti-CTL4). The anti-PD-1, anti-PDL-1 or anti-CTLA4 may be nivolumab, pembrolizumab, cemiplimab, atezolizumab, avelumab, durvalumab, ipilimumab or tremelimumab.

The cell, e.g. T cell, expressing the CAR molecule specific of IL-1RAP is therefore useful in a method to treat AML in a human, wherein the human has already received a graft-versus-leukemia, an allogenic stem cell transplantation, a donor lymphocytes infusion (DLI), a previous CART-cells therapy which is not a IL-1RAP CART-cells or a hematopoietic transplantation allogeneic or autologous.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

Thus, the present disclosure provides a method for the treatment of AML comprising administering to a subject in need thereof, a therapeutically effective amount of a cell comprising a nucleic acid molecule encoding a chimeric antigen receptor (CAR), wherein the CAR comprises an antibody or antibody fragment which includes an anti-IL-1RAP binding domain, a transmembrane domain, and an intracellular signaling domain comprising at least a stimulatory domain, and wherein said anti-IL-1RAP binding domain comprises:

(i) a light chain comprising a complementary determining region 1 (CDR1) having at least 80% identity with the amino acid sequence SEQ ID NO: 6, a complementary determining region 2 (CDR2) having at least 80% identity with the amino acid sequence SEQ ID NO: 7 and a complementary determining region 3 (CDR3) having at least 80% identity with the amino acid sequence SEQ ID NO: 8, and (ii) a heavy chain comprising a complementary determining region 1 (CDR1) having at least 80% identity with the amino acid sequence SEQ ID NO: 12, a complementary determining region 2 (CDR2) having at least 80% identity with the amino acid sequence SEQ ID NO: 13 and a complementary determining region 3 (CDR3) having at least 80% identity with the amino acid sequence SEQ ID NO: 14.

The cells, e.g. T cell, may be administered either alone, or as a pharmaceutical composition in combination with diluents and/or with other components such as IL-2 or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The cell for use according to the invention may be formulated in a composition.

Thus, the invention also relates to a composition, such as a pharmaceutical composition, comprising a cell, said cell comprising a nucleic acid molecule encoding a chimeric antigen receptor (CAR), for use in the treatment of acute myeloid leukemia (AML), wherein the CAR comprises an antibody or antibody fragment which includes an anti-IL-1RAP binding domain, a transmembrane domain, and an intracellular signaling domain comprising at least a stimulatory domain, and wherein said anti-IL-1RAP binding domain comprises:

(i) a light chain comprising a complementary determining region 1 (CDR1) having at least 80% identity with the amino acid sequence SEQ ID NO: 6, a complementary determining region 2 (CDR2) having at least 80% identity with the amino acid sequence SEQ ID NO: 7 and a complementary determining region 3 (CDR3) having at least 80% identity with the amino acid sequence SEQ ID NO: 8, and (ii) a heavy chain comprising a complementary determining region 1 (CDR1) having at least 80% identity with the amino acid sequence SEQ ID NO: 12, a complementary determining region 2 (CDR2) having at least 80% identity with the amino acid sequence SEQ ID NO: 13 and a complementary determining region 3 (CDR3) having at least 80% identity with the amino acid sequence SEQ ID NO: 14.

Compositions for use according to the present invention are preferably formulated for parenteral administration, e.g., intravascular (intravenous or intraarterial), intraperitoneal or intramuscular administration.

"administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion.

In one embodiment, the CAR-modified cells or the compositions are administered to a subject by direct injection into a tumor, lymph node, systemic circulation, or site of infection.

In one embodiment, the CAR-modified cell, e.g. CAR-modified T cell, are useful to treat a subject diagnosed with AML, by removing immune effector cells from the subject, genetically modifying said immune effector cells with a vector comprising a nucleic acid encoding a CAR as described herein, thereby producing a population of modified immune effector cells, and administering the population of modified immune effector cells to the same subject. In a preferred embodiment, the immune effector cells comprise T cells.

The quantity, frequency of administration and the sequence of the possible association with conventional AML treatments will be determined by such factors as the condition of the patient, and the type and severity of the AML, although appropriate dosages may be determined by animal models and finally by clinical trials.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges.

The invention is further described in detail by reference to the following experimental examples. These examples are provided for purposes of illustration only, and are not intended to be limiting unless otherwise specified.

EXAMPLES

Example 1: Monoclonal Antibody Production

A mouse anti-hIL-1RAP monoclonal antibody was generated by standard hybridoma technique.

Briefly, BALB/c mice (5 weeks, Charles River) were immunized either by foot pad (n=3) or intraperitoneally (n=5) with a recombinant fusion protein consisting of the extra cellular part of IL-1RAP (NM_002182.2, NCBI) and the Fc-part of human IgG1 (R&D Systems, Lille, France). Lymph nodes or spleens cells and blood samples were harvested and cells were fused with the mouse myeloma cell line, then screened by FACS analysis Becton Dickinson)(, against IL-1RAP-positive (KU812) and -negative (Raji, KG1) cell lines.

Screening of hybridoma allowed to select 5 monoclonal antibodies subclones that discriminate IL-1RAP positive (KU812 or KG-1 respectively AML or $Phi^{+}p^{210}$ CML) from negative cell lines (Tom-1, NALM-20, Jurkat or Raji, respectively $Phi+^{p190}$ B-ALL, $Phi^{-}$B-ALL, T-ALL or Burkitt's lymphoma).

Molecular Characterization of Antibodies

Molecular characterization was performed by Sanger sequencing of cloned PCR products amplification obtained with degenerated primers specific of the FR1 and constant regions of the heavy and light chains according to the protocol of Wang. Z. et al (J. Immunol. Methods, 2000; 233, pages 167-77). Identification of V-D-J-C gene rearrangement and CDR3 region was obtained after alignment of consensus nucleotide sequences against the IMGT® database using V-QUEST online tool according to Brochet X., et al. (Nucleic Acids Res., 2008, 36, pp 503-8). Molecular Sanger sequencing showed that all of the 5 monoclonal antibodies are identical and share the same CDR3 nucleotide sequences. The monoclonal antibody subclone (#E3C3) was chosen, since it gave the highest relative fluorescence intensity (RFI) by cytometry.

Selected antibody (clone #E3C3) was characterized by western blotting, ELISA against recombinant IL-1RAP protein, immunohistochemistry, confocal microscopy, tissue micro array (TMA) from normal tissues (FDA normal human organ tissue array, 99 cores/33 sites/75 cases) and primary samples of CML patients.

Western Blotting of Subcellular Fractions (FIG. 1)

Whole cellular lysates of different AML or CML (positive control) hematopoietic cell lines were separated by polyacrylamide gel electrophoresis and electrotransferred onto polyvinylidene difluoride membranes. Membranes were probed overnight with primary IL-1RAP #A3C3 (diluted at 1:20). Twenty micrograms of protein were electrophoresed on sodium dodecyl-sulfate polyacrylamide gels (SDS-PAGE), and then sonicated protein fractions were suspended in RIPA buffer supplemented with a protease inhibitor cocktail (complete Mini EDTA-free; Roche, Bale, Switzerland). Protein load in the western blot lane was evaluated with β-actin mAb staining (1:1000, clone AC15, #A5441, Sigma-Aldrich). Immunodetection staining was performed with a secondary polyclonal antibody sheep anti-mouse IgG (#515-035-062, Jackson). Enhanced chemiluminescence detection reagents allowed detection with a camera and Bio-1D software (Vilber-Lourmat, Collegien, France).

Figure 18:
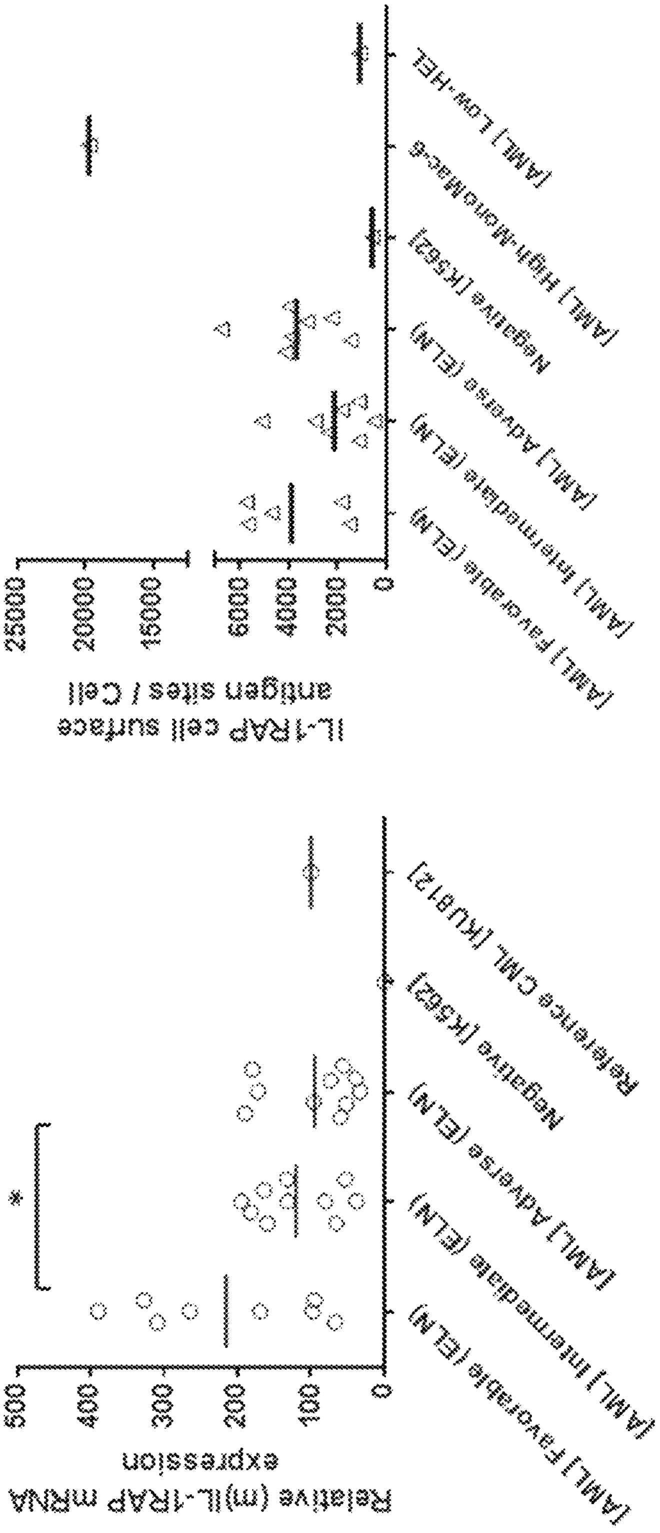
FIG. 18: IL-1RAP mRNA expression and absolute cell surface IL-1RAP antigen sites on primary samples of AML patients according to the European Leukemia Net (ELN) prognosis classification.

Relative IL-1RAP mRNA Expression (FIG. 18)

Relative IL-1RAP mRNA expression was determined by RT-qPCR using the Hs_00895050_ml Taqman qPCR gene expression assay (ThermoFisher Scientific) targeting the mRNA variant codon for the cell surface protein. Analysis was performed on whole blood or bone marrow samples from AML patients (n=29) at diagnosis, according the European Leukemia Net (ELN) prognosis classification. K562, MonoMac-6 and HEL-60 mRNA were used respectively as negative, high or low positive controls.

Figure 3:
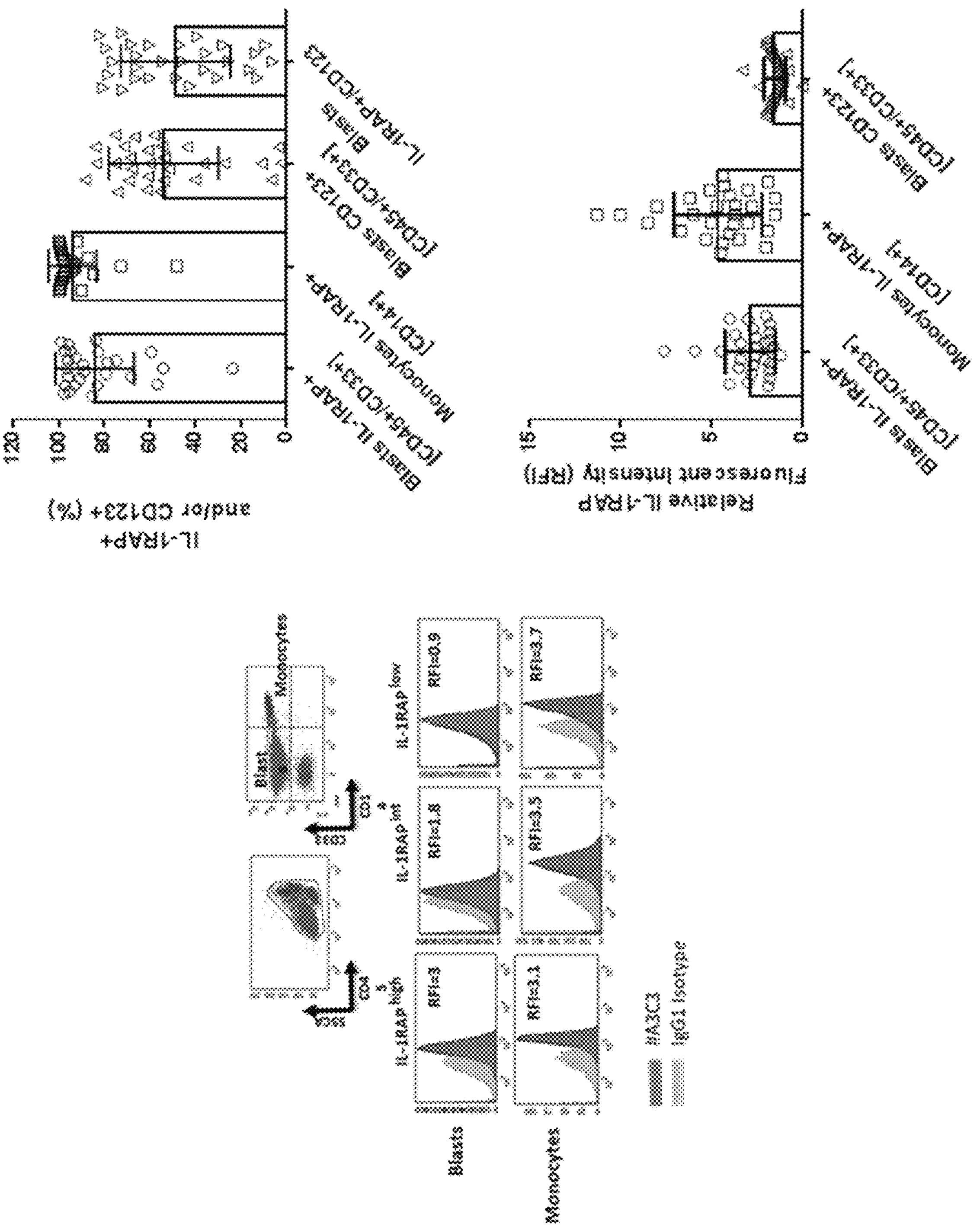
FIG. 3: Flow cytometry-gating strategy on AML primary samples of patients. RFI is provided for blasts and monocytes subpopulations (Left). Percentage of IL-1RAP+ within AML blasts and monocytes, CD123+ and IL-1RAP+/CD123+ cells within AML Blasts in a cohort of routine AML (all subtypes) patients (n=30) (Right, up). RFI is also provided (Right, bottom).

Absolute Number of IL-1RAP Antigenic Sites (FIG. 3)

The determination of the absolute number of IL-1RAP antigenic sites was based on the Cytometric Bead Arrays (CBA) technique. Different leukemia lines at $1 \cdot 10^{6}$ cells/mL were labelled with a primary anti-IL-1RAP antibody (unlabeled #A3C3, Diaclone®) and revealed with a FITC-IgG1 anti mouse secondary antibody (Catalog #: 55526, MP Biomedicals®). Experiment was performed with the Cell Quant Calibrator kit, following recommendation (Ref 7208, Biocytex). An unlinked IgG1 isotypic was used as control (Catalog No 857-073-020, Diaclone). Analysis was done using flow cytometry (FACS Canto™ II, analysis of results with BD FACS DIVA V 7.0, BD Biosciences). KU812 and K562 were used respectively as positive and negative controls.

Figure 2:
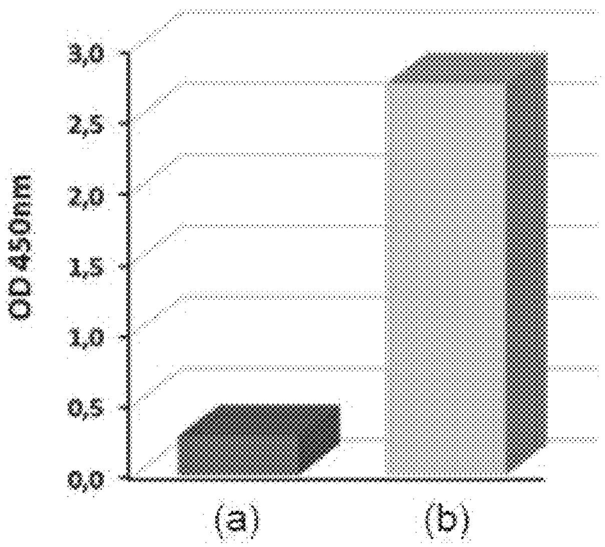
FIG. 2: recognition of IL-1RAP recombinant protein with #E3C3 mAb by the ELISA technique (b). BSA is the negative control (a).

In Vitro Detection of Recombinant IL-1RAP Protein Via ELISA (FIG. 2)

Anti-human Fc antibody was coated on a bottom of a plastic ELISA plate. IL-1RAP protein loaded on human antibody was probed with the murine and human IL-1RAP (#E3C3) antibody, revealed then by an anti-mouse FC antibody coated with horseradish peroxidase (HRP).

The ELISA confirms that #E3C3 monoclonal antibody recognize the IL-1RAP recombinant protein.

Flow Cytometry Analysis on Primary Cells from AML Patients (FIG. 3)

IL-1RAP cell surface staining of different hematopoietic AML cell lines was performed, using #A3C3 mAb and IL-1RAP murine mAb as staining comparison.

Relative Fluorescence Intensity (RFI) between IL-1RAP staining and isotype was calculated. IL-1RAP+(KU812) or IL-1RAP− (Raji) cell lines were used as positive or negative controls respectively.

For primary samples of bone marrow or peripheral bloods of AML patients, the murine IL-1RAP mAb (#E3C3) was included in a panel allowing to detect CD45, CD34, CD38, CD33, CD123, and CD14 (for monocytes). Stained cells were collected by a CANTO II cytometer (BD Biosciences, Le Pont-de-Claix, France) and analyzed by DIVA 6.1 software (BD Biosciences, Le Pont-de-Claix, France).

Detection In Situ

In order to study specific or non-target tissue binding, FDA standard frozen tissue arrays, including 90 tissue cores (30 organs) of 3 individual donors per organ (US Biomax, Rockville, United States) were incubated as previously described. Immunostaining was detected using UltraView Universal DAB Detection Kit (Ventana, USA). Images were acquired and analyzed with NDP.view 2 software. High IL-1RAP (KU812) or negative (Raji) expressing cell lines were respectively used as positive or negative controls. The staining intensity was graduated as follows: negative (0), weak staining (1+), moderate staining (2+), or strong staining (3+). High IL-1RAP (KU812) or negative (Raji) expressing cell lines were respectively used as positive or negative controls.

Figure 4:
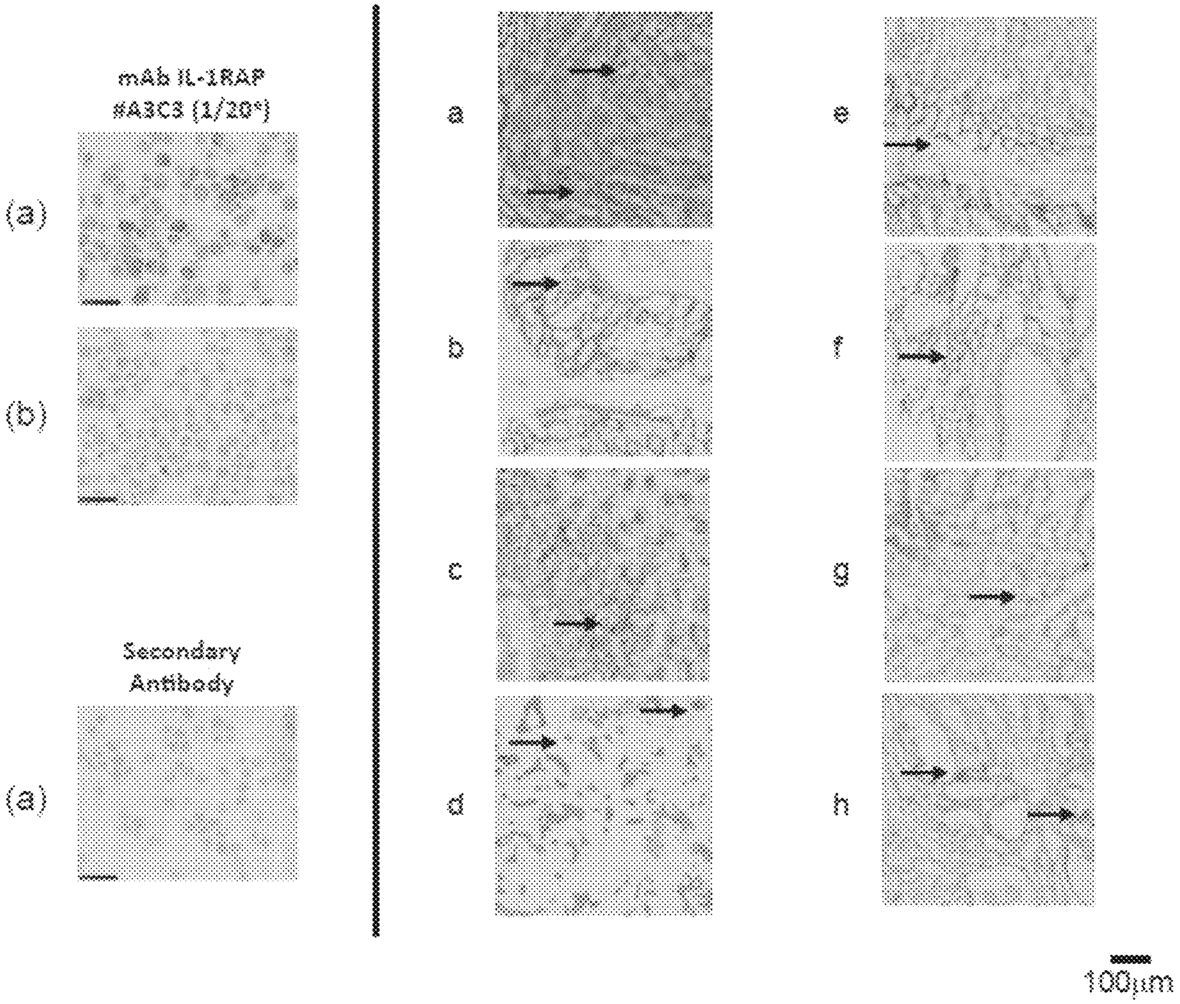
FIG. 4: Specific tissue binding using frozen tissue array. High IL-1RAP (KU812) (a) or negative (Raji) (b) expressing cell lines were respectively used as positive or negative controls. The following tissues have been tested a: Lymph node, b: colon, c: small intestine, d: placenta, e: stomach f: lung, g: spleen and h: prostate.

IL-1RAP expression has been investigated using #E3C3 monoclonal antibody. Staining was detected in only 6 tissues as Lymph node, colon, small intestine, placenta, stomach and prostate, mainly epithelial or endothelial cells at various intensities (FIG. 4).

Results

#A3C3 is able to stain different AML cell lines expressing IL-1RAP at the cell surface. With #A3C3, by western blotting, we therefore confirmed IL-1RAP expression at the cell surface of different cell lines, with a signal of different intensity levels. Interestingly CD14+ monocytes subpopulation expressed also IL-1RAP. By flow cytometry analysis of AML (all subtypes, n=30) patient's cohort, we confirmed, as previously shown in the prior art, the presence of IL-1RAP on AML blasts at various percentages (84.27±17.4%) and cell surface level expressions, although monocytes expression level remain stable. It was confirmed also by absolute counts of IL-1RAP antigen sites on AML patients classified with the European Leukemia-Net (ELN) prognosis stratification. Based on these results, we defined 3 different cell surface expression levels: low, intermediate and high. These levels of expression were modeled by cell lines for further studies.

Example 2: Lentiviral Constructs

Based on molecular sequencing of VDJ or VJ rearrangements and CDR3 nucleotide sequence determination, CAR lentiviral construct (pSDY-iC9-IL-1RAPCAR-dCD19) was prepared by cloning the synthetically produced single chain Fragment variable (scFv) derived from the #E3C3 IL-1RAP hybridoma of example 1 into the SIN-pSDY backbone (Rossolillo P, Winter F, Simon-Loriere E, Gallois-Montbrun S, Negroni M. Retrovolution: HIV-driven evolution of cellular genes and improvement of anticancer drug activation. PLoS Genet. 2012; 8(8):e1002904).

Briefly, a SIN lentiviral construct carrying a safety cassette iCASP9, the single chain fragment variable of #E3C3 monoclonal antibody) and a cell surface expressed marker ΔCD19 for monitoring and potential cell selection has been constructed. All of these 3 transgenes are separate by 2A peptide cleavage sequences and under control of EF1 promoter and SP163 enhancer sequence (part of the 5'UTR of the mouse VEGF gene, GenBank accession #U41383).

Figure 5:
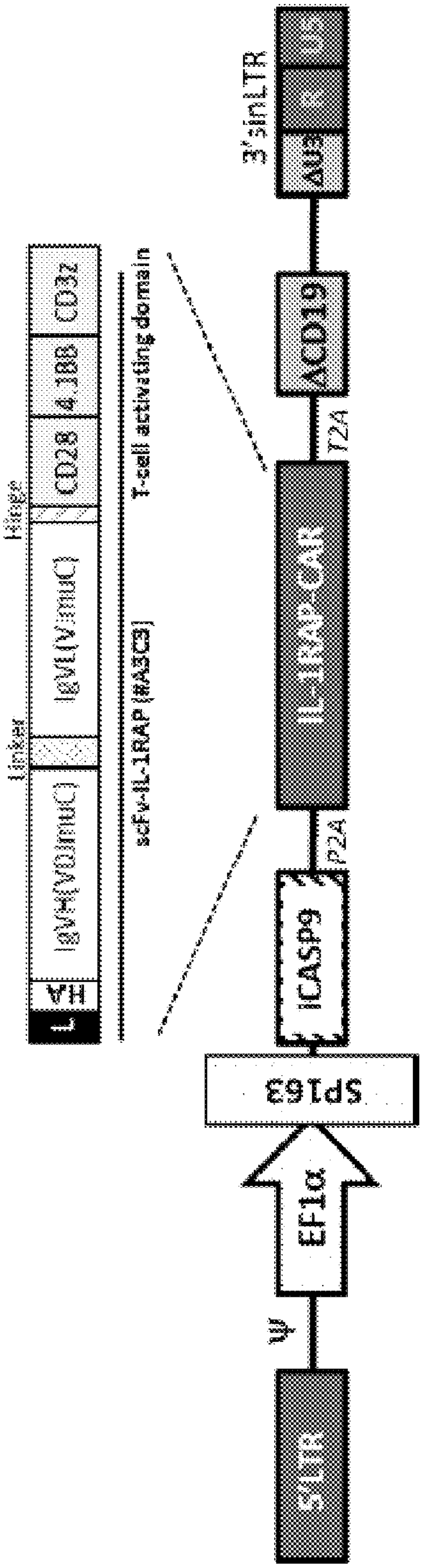
FIG. 5: Design of a SIN lentiviral construct carrying a safety cassette iCASP9, the single chain fragment variable (scFv) of #E3C3 mAb and a cell surface expressed marker ΔCD19. The 3 transgenes are separated by 2A peptide cleavage sequences and under control of EF1 promoter plus SP163 enhancer sequence.

As seen in FIG. 5, the construct carries 3 different parts as a suicide safety cassette iCASP9 (chemical inducible Caspase 9), the IL-1RAP CAR and a cell surface and selection marker as ΔCD19 (CD19 truncated of the intracellular part avoiding signaling), separate by 2 different 2A ribosomal skip sequences (P2A and T2A) under control of EF1a (Elongation Factor 1 promotor alpha) promoter added of the SP163 enhancer. The scFv, constituted of the variable regions of the Heavy (VH) and Light (VL) sequence chains of #E3C3 immunoglobulin, is cloned in frame with the CD28-4.1BB-CD3z signaling chain and under control of the EF1a promoter and the SP163 enhancer. The IL-1RAP CAR contains of single chain variable fragments (scFv), associated with a leader sequence (L), tagged with Human influenza hemagglutinin (HA) and connected through a hinge region to T cell activating domain consisting of 2 co-stimulatory domains (modified transmembrane and intracellular signaling CD28 and 4-1BB) and the CD3z intracellular signaling domain. Mock T consists of the same construct without IL-1RAP scFv.

Example 3: Generation of IL-1RAP CART cell

CD3+T lymphocytes obtained from healthy donors peripheral blood mononuclear cells were activated with anti-CD3/CD28 beads (Life Technologies, France) according to the manufacturer's instructions, and then isolated over a magnetic column (MACS, Miltenyi Biotec, Paris, France). On day 2, activated T cells were transduced by spinoculation using lentiviral vectors of Example 2, in contact of the supernatant (SN), at 2000 g for 90 min at 10° C. Transduction efficiency was determined by performing flow cytometric analysis to identify ΔCD19 cell surface marker expression. Four days after transduction, CD19 positive cells labeled with CD19 microbeads (Miltenyi Biotec, Paris, France) were magnetically separated using a MACS Column The isolated CD19 expressing cells were expanded in complete X-vivo® medium (Lonza, Bale, Suisse) containing 500 UI/mL rhIL-2 (Proleukin; Novartis), supplemented with 8% human serum and cryopreserved. Experimentally, we used TransAct™ T Cell Reagent and TexMACS™ Medium (Miltenyi Biotec, Paris, France) supplemented with Human IL-2; IL-7, IL-15 or IL-7+IL-15.

Example 4: Lentiviral Transduction of Donor T Cells

Lentiviral vector supernatant stocks of Example 2 were produced by transient co-transfection of sub-confluent 293T cells using CaCl2) method with helper plasmids encoding vesicular stomatitis virus (VSV) envelope (pMDG), and the GAG/POL (psPAX2) packaging plasmids (Addgene, respectively #12259 and #12260, Trono et al, Lausanne, Switzerland) Viral supernatant was harvested 48 and 72 hours later, concentrated using PEG and low speed centrifugation (3000 g, overnight), then stored at −80° C. until use. The same lentiviral construct (Mock) without IL-1RAP scFv was used as control. Titration of the lentiviral supernatant was established by 293T permissive cells transduction using serial dilution of SN.

Transduction efficiency was measured by flow cytometry. Multiplicity of infection (MOI) was deducted from supernatant titration according to the number of starting cells.

In vitro production process with lentiviral supernatant allows transducing primary T cells respectively at MOI of 2 for Mock or CAR IL-1RAP supernatant.

Western Blot Analysis of IL-1RAP CAR Expression.

Figure 6:
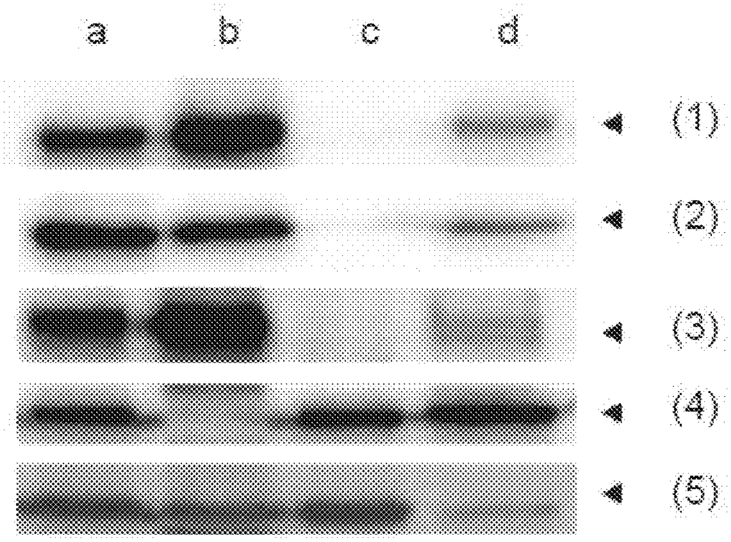
FIG. 6: CD3 western blotting on subcellular fractions of IL-1RAP transduced T cells. a: total lysate, b: membrane, c: cytoplasm, d: nucleus, (1) CAR associated CD3zeta (55 kDa), (2) endogenous CD3zeta (16 kDa), (3) CD45 (147 kDa), (4) lamin (68 kDa), (5) GAPDH (35 kDa).

Whole protein lysate or protein extracted from membrane or cytoplasm cellular sub-fractions (obtained after ultracentrifugation) of IL-1RAP transduced T cells were probed with a mouse anti-human CD3z antibody. Western blotting on subcellular fractions showed that the IL-1RAP CAR is associated with CD3z signaling (signal at 55KDa compared to the expected endogenous CD3z signal at 16KDa) (FIG. 6).

Analysis by Flow Cytometry

CAR expression at T cell surface analyzed using the recombinant IL-1RAP biotinylated protein and revealed by flow cytometry using a secondary anti-biotin antibody (Miltenyi Biotec Clone #Bio3-18E7). CEM cell line or primary T cells were transduced either with Mock or CAR IL-1RAP. Cells were then incubated in presence of increasing amount of recombinant IL-1RAP labelled with biotin. Staining was performed with an anti-biotin fluorescent antibody and analyzed by flow cytometry. Percentage of Biotin+/CD19+ CEM or T-cells plotted against amount of labelled biotin recombinant protein. Dot plots of cytometry analyze were provided for representative staining, including maximum. Untransduced T cells (C0) or Mock T cells were used as control.

Figure 7:
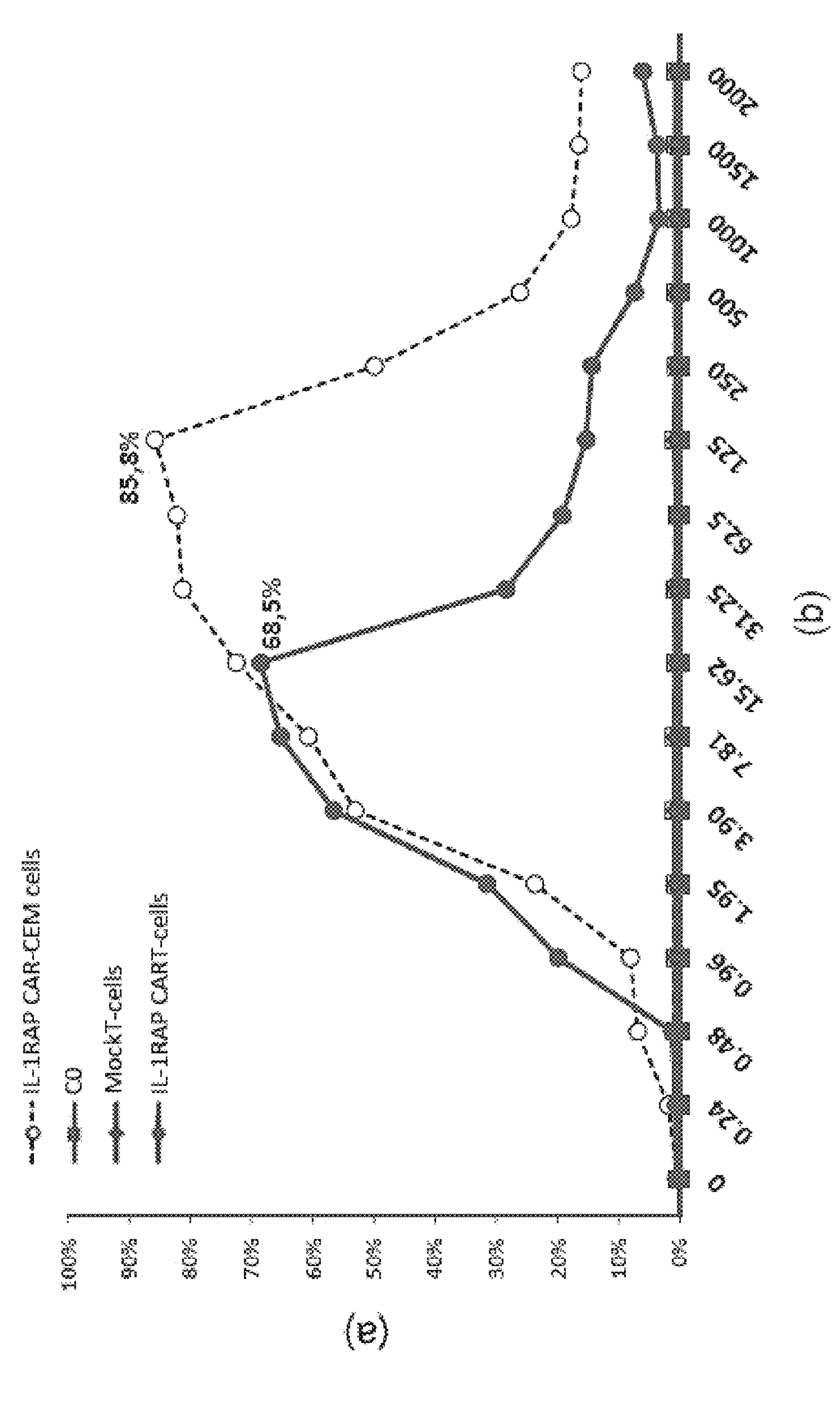
FIG. 7: FACS analysis detection of either IL-1RAP CAR transduced CEM T cell line or primary T-cells. Percentage of Biotin+/CD19+ CEM or T-cells (a) were plotted against amount of labelled biotin recombinant protein (b).

Additional analysis using serial dilution of biotinylated IL-1RAP protein (from 20 ng to 2.4 pg/ml) and FACS analysis allow to detect either IL-1RAP CAR transduced CEM T cell line or primary T-cells. Single experiment allow to show that different amounts of recombinant protein, as 1.25 ng and 0.15 ng are respectively required for recruiting maximum of CEM (85.8%) or primary (68.5%) GMTC (FIG. 7).

More CAR are expressed at the cell surface of CEM than primary T cells. Moreover, addition of high amount (1000 time>plasmatic concentration) of cold recombinant IL-1RAP protein in E:T co-culture lead to a significate inhibition of the effector cytotoxicity.

These experiments confirm that CAR is addressed at the cell surface and that there is a CAR specific recognition and binding of IL-1RAP protein.

Example 5: Efficiency of the Safety Suicide Gene iCASP9 Cassette

Transduced (IL-1RAP CAR 293T) or untransduced (293T) cells were cultured in media alone (Chemical Inducer Dimerizer (CID)) or media containing 20 nM of CID AP1903 for 24h. Light microscopy allows to image the presence and architecture of the live or death cells in culture (×40).

Figure 8:
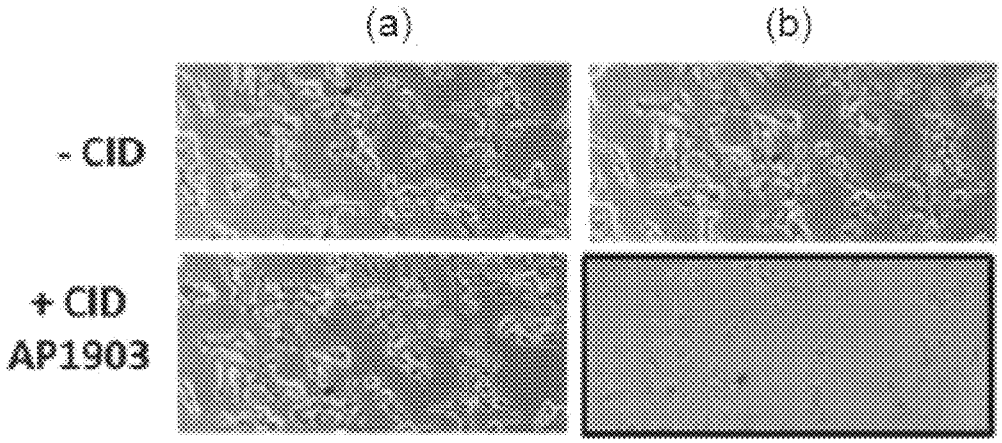
FIG. 8: Safety switch of the iCASP9/AP1903 suicide system cassette after Chemical Inducer Dimerizer (10 nM CID) exposure. (a) 293T cells, (b) IL-1RAP CAR 293T cells

By optical microscopy, it can be shown that 293T cells culture transduced by IL-1RAP CAR is sensitive to the CID (FIG. 8).

Flow cytometry analysis after CID exposure (20 nM, 24h) or not (light grey) on untransduced T cells (C0) and on GMTC cells mixture, expressing or not IL-1RAP CAR. $CD3^+/CD19^+$ staining allow discriminating GMTC expressing CAR from the others.

Untransduced T cells (C0) or IL-1RAP CART Cells were both exposed to medium alone or medium +CID (20 nM, 24h).

Figure 9:
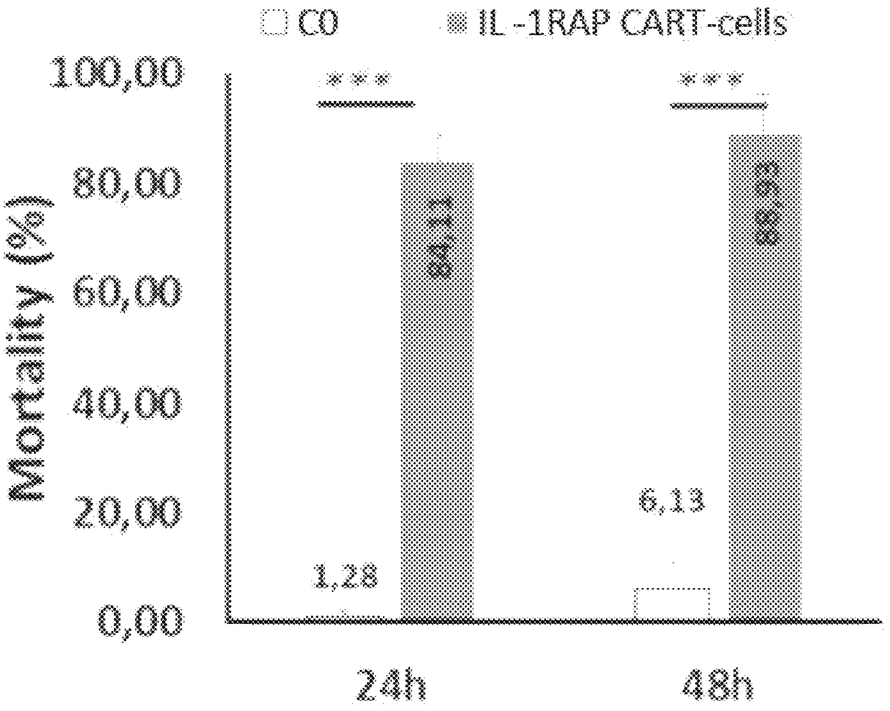
FIG. 9: elimination of IL-1RAP CART cells after 24 h or 48 h CID exposure compared to untransduced T cells (C0) (*** $p<0.001$, n=3).

Precise cell death was first assessed by flow cytometry after Annexin-V/7-AAD gating according to the manufacturer's instructions (Beckman Coulter, IM3614). Fluorescence analysis was gated on $CD3^+/CD19^+$ positive cells. The quantification was determined with after acquiring 5000 fluorescent beads. Killing efficiency was normalized against control cells (untreated cells). Cell killing was calculated as follows: % Dead cells=[1-(absolute number of viable cells in AP1903-treated cells/absolute number of viable cells in untreated cells)]×100. 24 h or 48 h C0 or IL-1RAP CART (gated on CD3+/CD19+) cells CID exposure. Results are showed as mean±SD from 3 independent experiments. *: p<0.001 (FIG. 9**).

Cytometry analysis show that after 24 h CID exposure of a mixed population of T cells expressing ($CD19^+$) or not ($CD19^-$) IL-1RAP CAR, only the $CD19^-CD3^+$ cells persist26. More precisely, using a quantitative AnnV/7AAD assay of apoptosis, we showed that 84.11% and 88.93% of IL-1RAP CART cells are eliminated after 24 h or 48 h CID exposure compared respectively to untransduced T cells (C0) (1.28% and 6.13% respectively at 24 h or 48h) (p<0.001, n=3).

Example 6: Proliferative Capability of IL-1RAP CART Cells

Materials and Methods

Untransduced T cells (C0), Mock-T cells (MockT) or IL-1RAP CAR (IL-1RAP CART) were cultured, for 3 days, at an Effector:Target (E:T) ratio of 1:3, either in medium alone (without targets) or in contact with IL-1RAP negative (K562) cells, or with cell surface expressing target cells (KU812, CML, positive control) and different IL-1RAP levels of cell surface expression (Low:HL-60; Intermediate: MOLM-13; High:EOL-1) AML cell lines. Effectors were previously labeled with 0.5·M CFSE without IL-2 supplementation. After 72 h of co-culture without IL-2 supplementation, divisions of living CD3+/CD19− (C0) and CD3+/CD19+ gated cells (MOCKT- or IL-1 RAP CART-cells) were assessed by flow cytometry to measure CFSE dye dilution.

Results

Figure 10A:
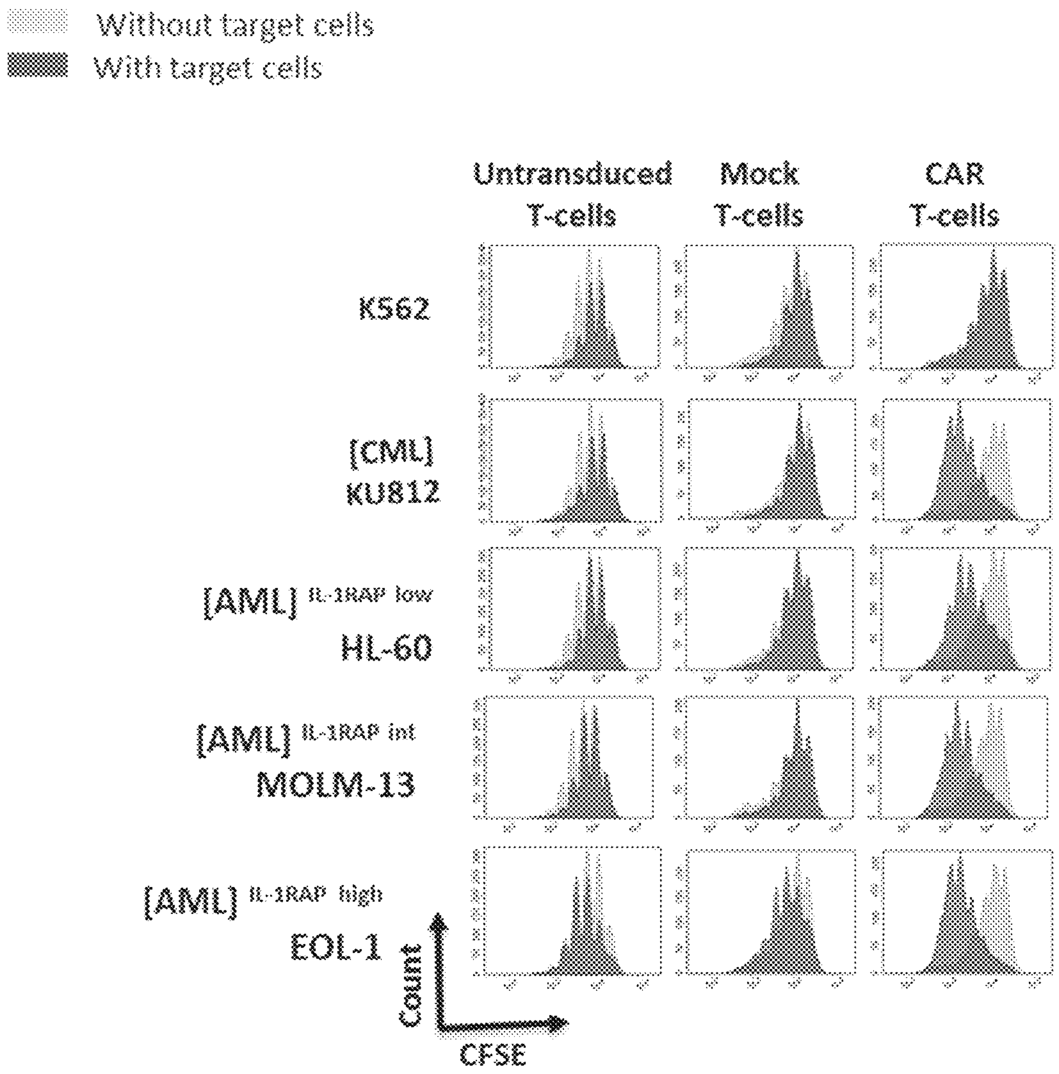
FIG. 10: (A) Gating strategy for flow cytometry CFSE dye dilution analysis, representative experiment. (B) Percentage of total dividing CFSE-positive cells. Mean±SD of 3 independent experiments. *** $p<0.001$ (Student test).
Figure 10B:
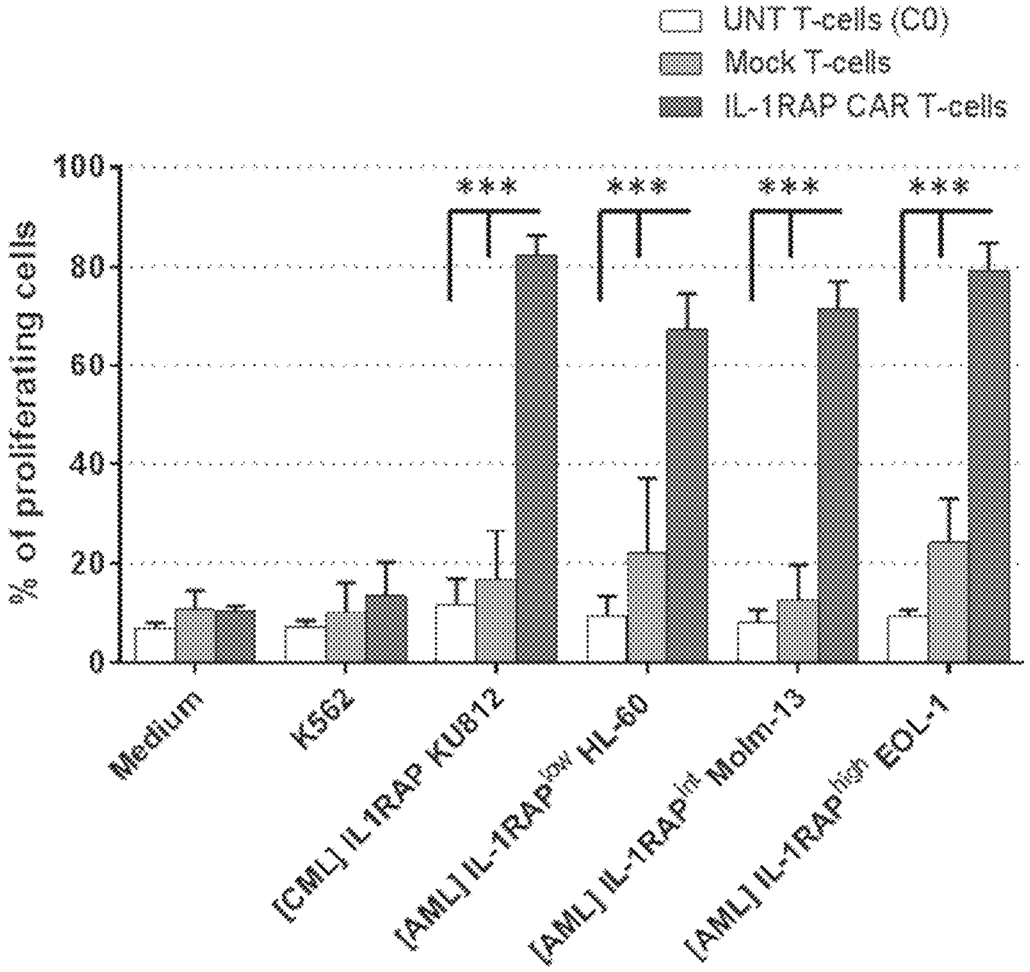

Contrary to untransduced T cells (C0) or MOCK transduced T-cells (MockT), IL-1RAP CART-cells were able to be activated and to divide specifically in presence of AML cell lines whatever the IL-1RAP cell surface expression of the target cells (FIGS. 10A et 10B).

Example 7: Intracellular Expression of IFNγ

Materials and Methods

Untransduced T cells (C0), Mock transduced T-cells (MockT) or IL-1RAP CAR (IL-1RAP CART) were cultured, for 6 hours, at an Effector:Target (E:T) ratio of 1:5, either in medium alone (without targets) or in contact with IL-1RAP negative (K562) cells, or with cell surface expressing target cells (KU812, CML, positive control) and different IL-1RAP levels of cell surface expression (Low: HL-60; Intermediate: MOLM-13; High: EOL-1) AML cell lines. As a positive control for cytokine production, cells stimulated with 10 ng/mL phorbol myristate acetate (PMA) and 1 μg/mL ionomycin (Sigma-Aldrich) were used as positive controls. IFNγ labeling was performed after brefeldin-A treatment and cell permeabilization. Fluorescent IFNγ signal was detected after gating on CD3+/CD19+ (CAR positives cells), in addition to CD8 staining, in order to differentiate CD8+ and CD4+ (formerly CD8−) cells.

Results

Figure 11A:
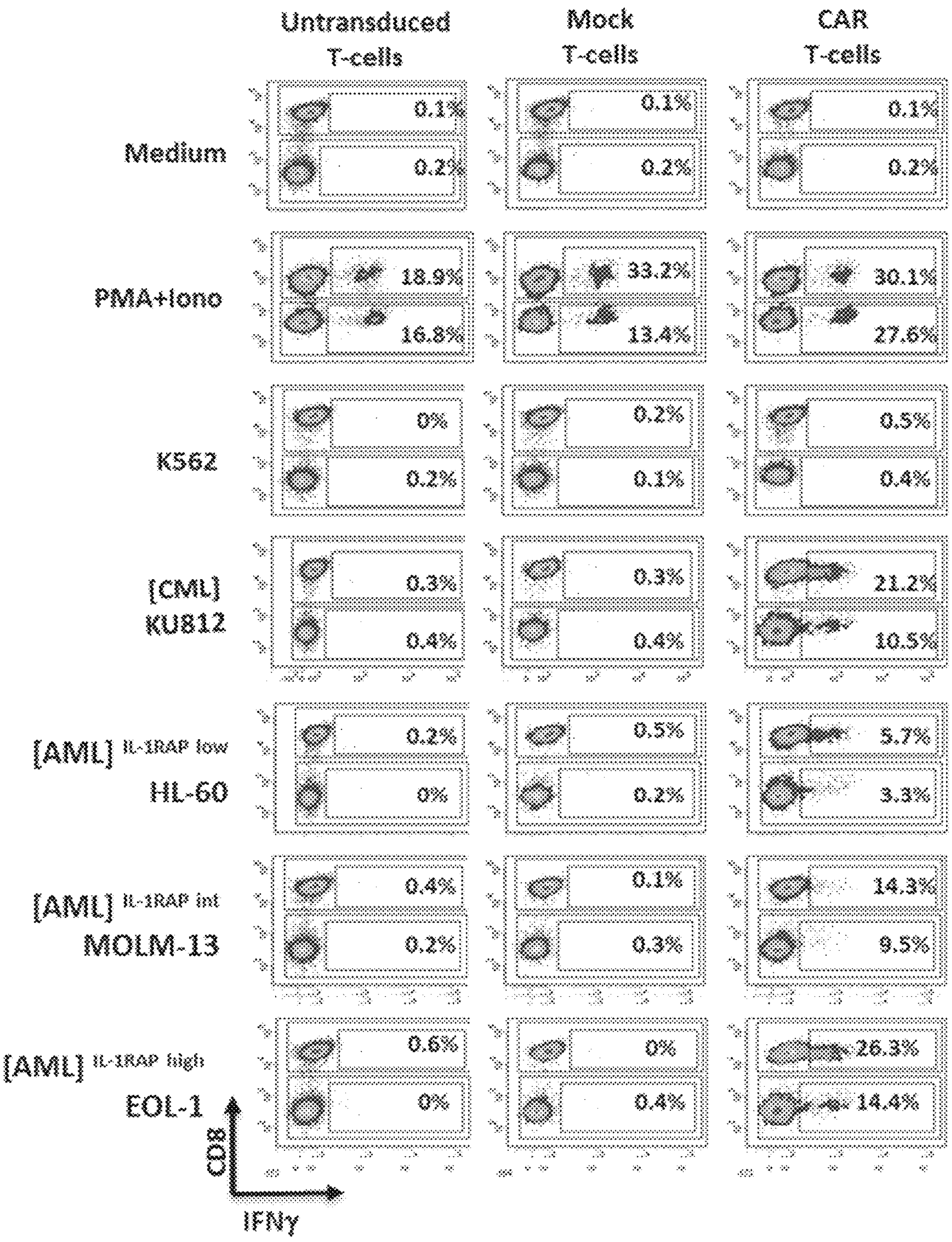
FIG. 11: (A) Gating strategy for intracellular IFNγ cytokine detection, representative experiment. (B) Percentage of total intracellular IFNγ-producing cells. Mean±SD of 3 independent experiments for CD8+ and CD8− (mainly CD4+) cells. * $p<0.001$.  $p<0.01$ (Student test)
Figure 11B:
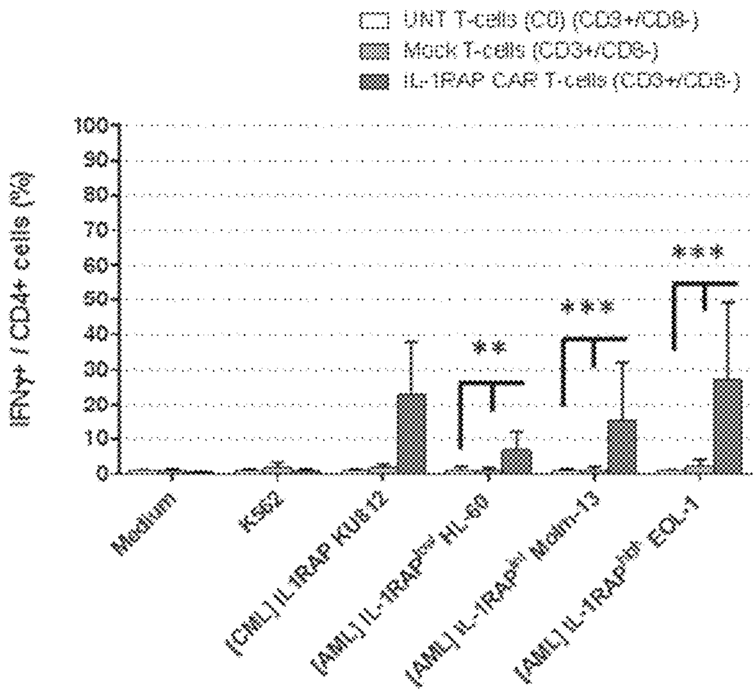
Figure 11B:
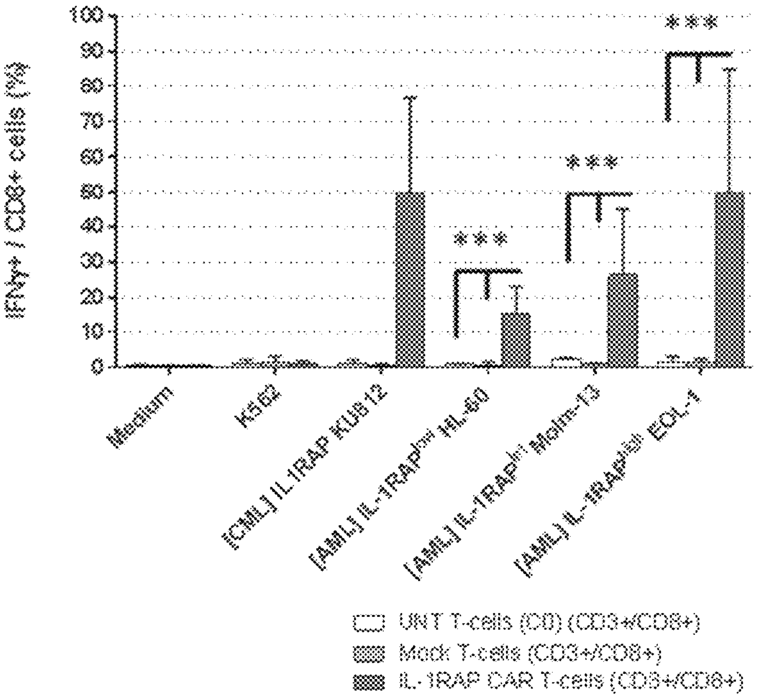

Contrary to untransduced T cells (C0) or MOCK transduced T-cells (MockT), CD8+ or CD4+IL-1RAP CART-cells are able to express intracellular IFNγ specifically in presence of AML cell lines whatever the IL-1RAP cell surface (FIGS. 11A and 11B).

Example 8: Cytoxicity of IL-1RAP CART-Cells Against AML Cell Lines

Materials and Methods

Effector cells were labeled with e-Fluor prior to co-culturing. Untransduced T cells (C0), Mock transduced T cells (MockT) or IL-1RAP CAR (IL-1RAP CART) were cultured, for 24 hours, at various Effector:Target (E:T) ratio, either in medium alone (without targets) or in contact with IL-1RAP negative (K562) cells, or with cell surface expressing target cells (KU812, CML, positive control) and different IL-1RAP levels of cell surface expression (Low: HL-60; Intermediate: MOLM-13; High: EOL-1) AML cell lines. Gating of cells against FSC and 7-AAD labeling allowed discrimination of target cells from effectors and from living cells. Percentage of persisting target cells in the presence or not of effector cells was determined in the gate FSC+/7-

AAD−. Untransduced T cells (C0) or mock-transduced T cells (MockT) were used as control.

Results

Figure 12A:
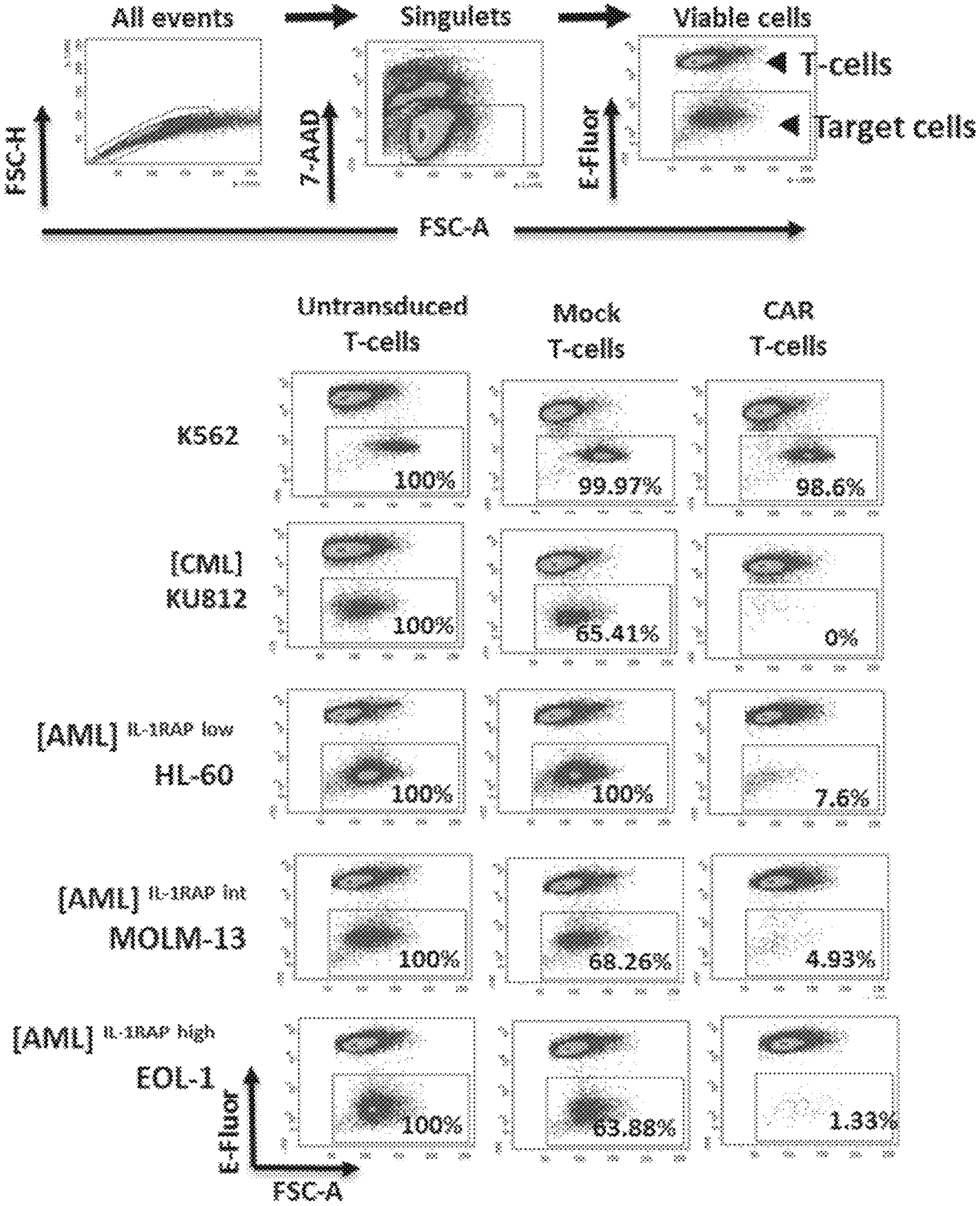
FIG. 12: (A) Gating strategy for efficacy study of IL-1RAP CAR T cells lysing cell surface IL-1RAP-expressing cells. (B) Percentage of total live target cells. Mean±SD of 3 independent experiments.
Figure 12B:
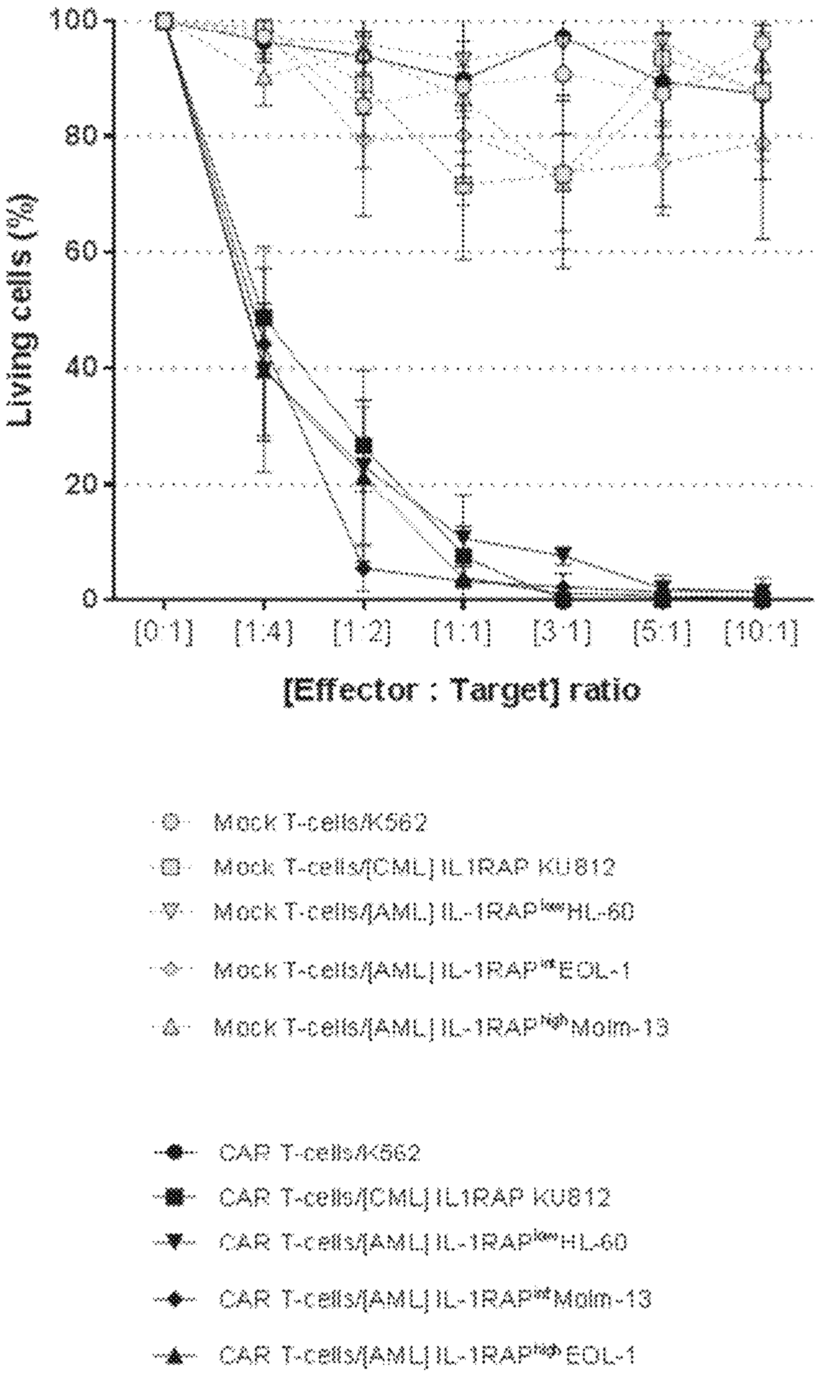

Contrary to MOCK transduced T-cells (MockT), co-culture of effectors CART cells with IL-1RAP positive targets (AML) at various E:T ratio allows to kill IL-1RAP expressing target AML cell lines with the same efficiency regardless level of tumor antigen expression (FIGS. 12A and 12B).

Figure 13A:
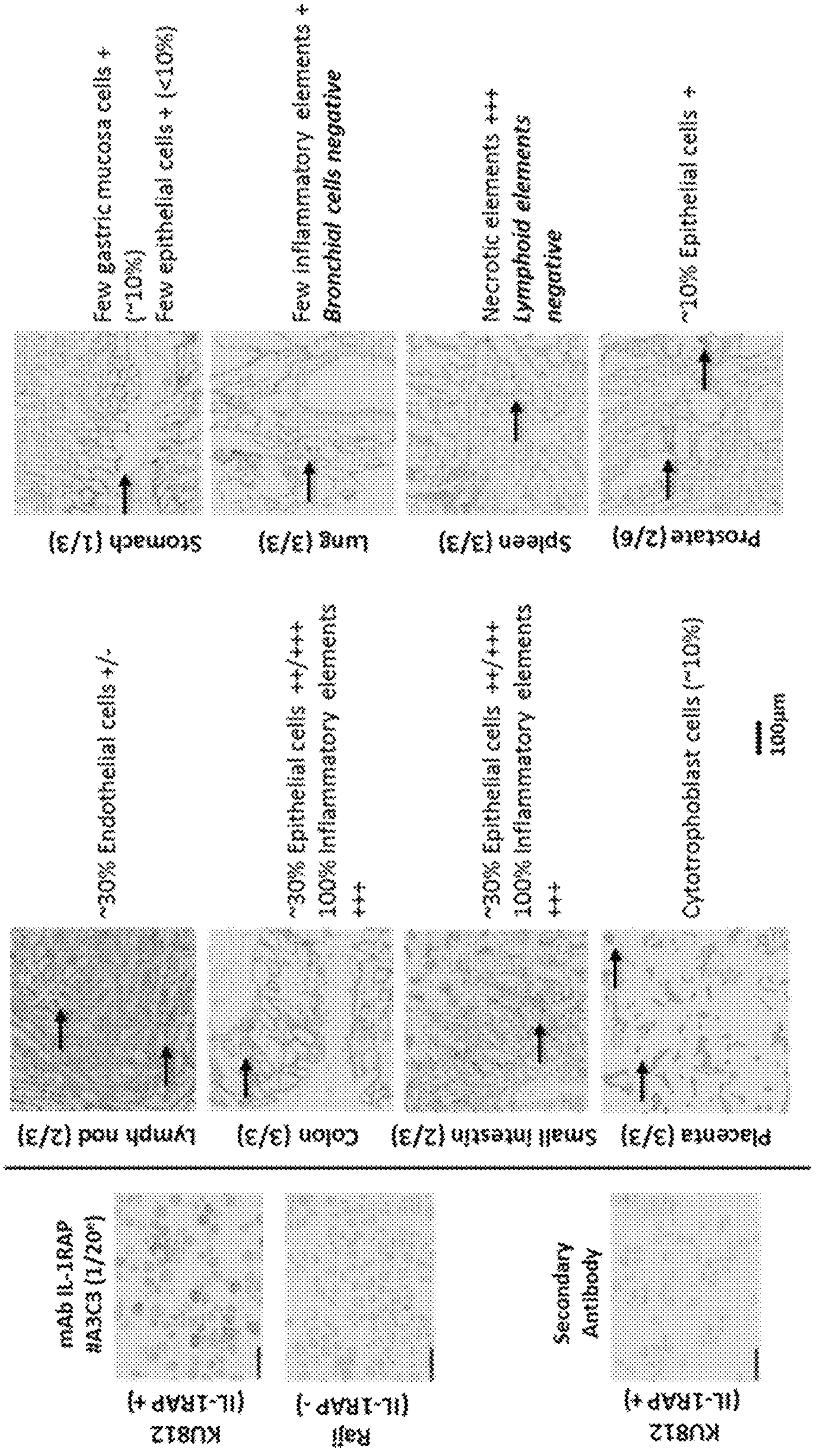
FIG. 13: (A) Tissue microarray. Representative #A3C3 staining of an US Food and Drug Administration standard frozen tissue array, including 90 tissue cores (30 organs) of 3 individual donors per organ (US Biomax, Rockville, MD, USA). Immunostaining was detected using the UltraView Universal DAB Detection Kit (Ventana, USA). Images were acquired and analyzed with NDP.view 2.0 software. Displayed are the tissues that showed some degree of staining with #A3C3 mAb in at least one individual out of three analyzed. (Scale bars, 100 μm.) High IL-1RAP (KU812) or negative (Raji)-expressing cell lines were respectively used as positive or negative controls. (B) IL-1RAP R&D (red) or #A3C3 (blue) staining of HMEC-1 dermal endothelial cell line. Isotype IgG1 (gray) is depicted as overlay. RFI is provided for both staining.
Figure 13B:
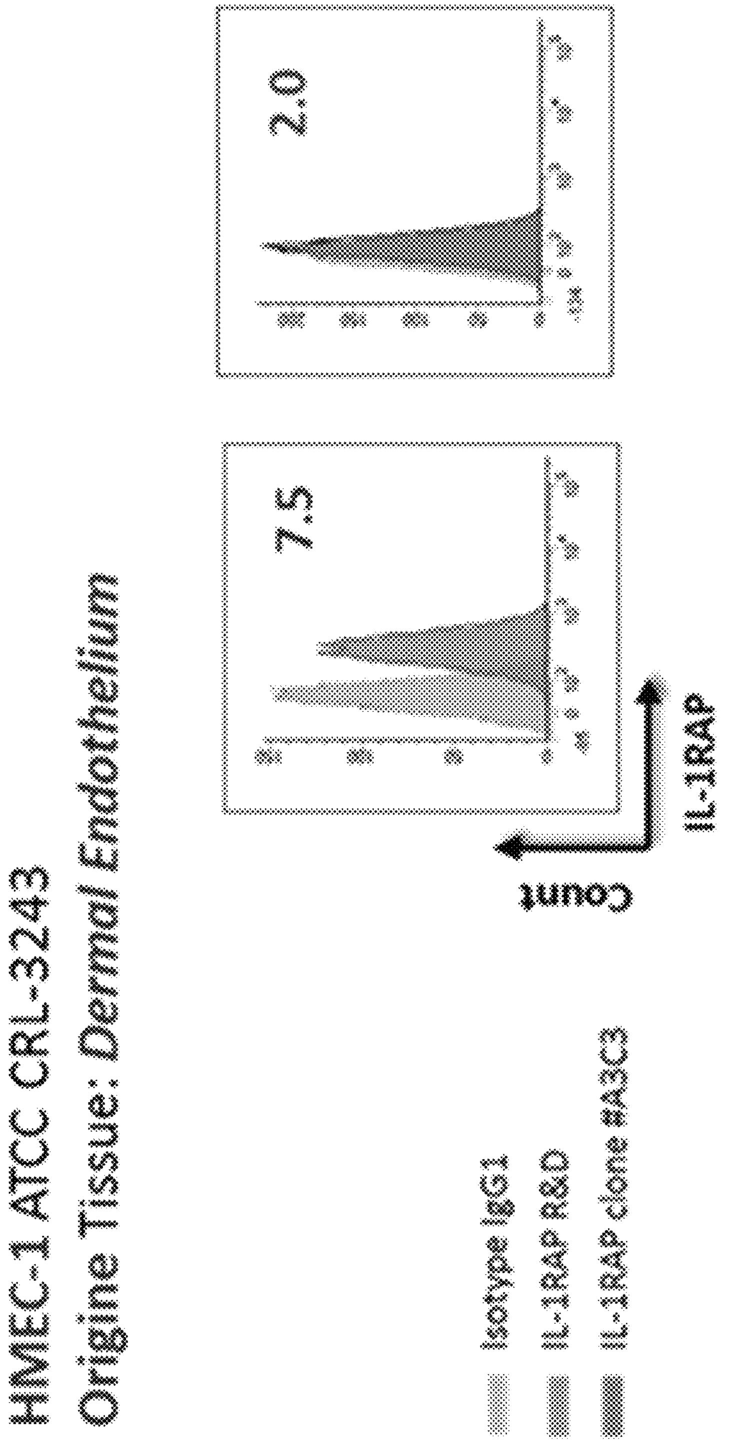

Example 9: IL-1RAP-CART Cells Secured by an iCASP9 Safety Switch have No Major Deleterious Effect on Healthy Hematopoietic Cells In order to predict off-target toxicity, we used the #A3C3 mAb to investigate IL-1RAP expression using a tissue macroarray (TMA) of 30 normal human tissues. Staining was detected at various intensity levels, excluding inflammatory or necrotic elements, in only six tissues: lymph node, prostate, skeletal muscle, stomach, colon and small intestine, and pancreas (FIG. 13A and Table 2). Interestingly, the microvascular HMEC-1 endothelial cell line was not recognized by our #A3C3 IL-1RAP mAb (FIG. 13B), whereas the R&D IL-1RAP mAb (R&D Systems—Ref #89412) clearly detects cell surface expression, suggesting recognition of a different epitope.

Figure 14A:
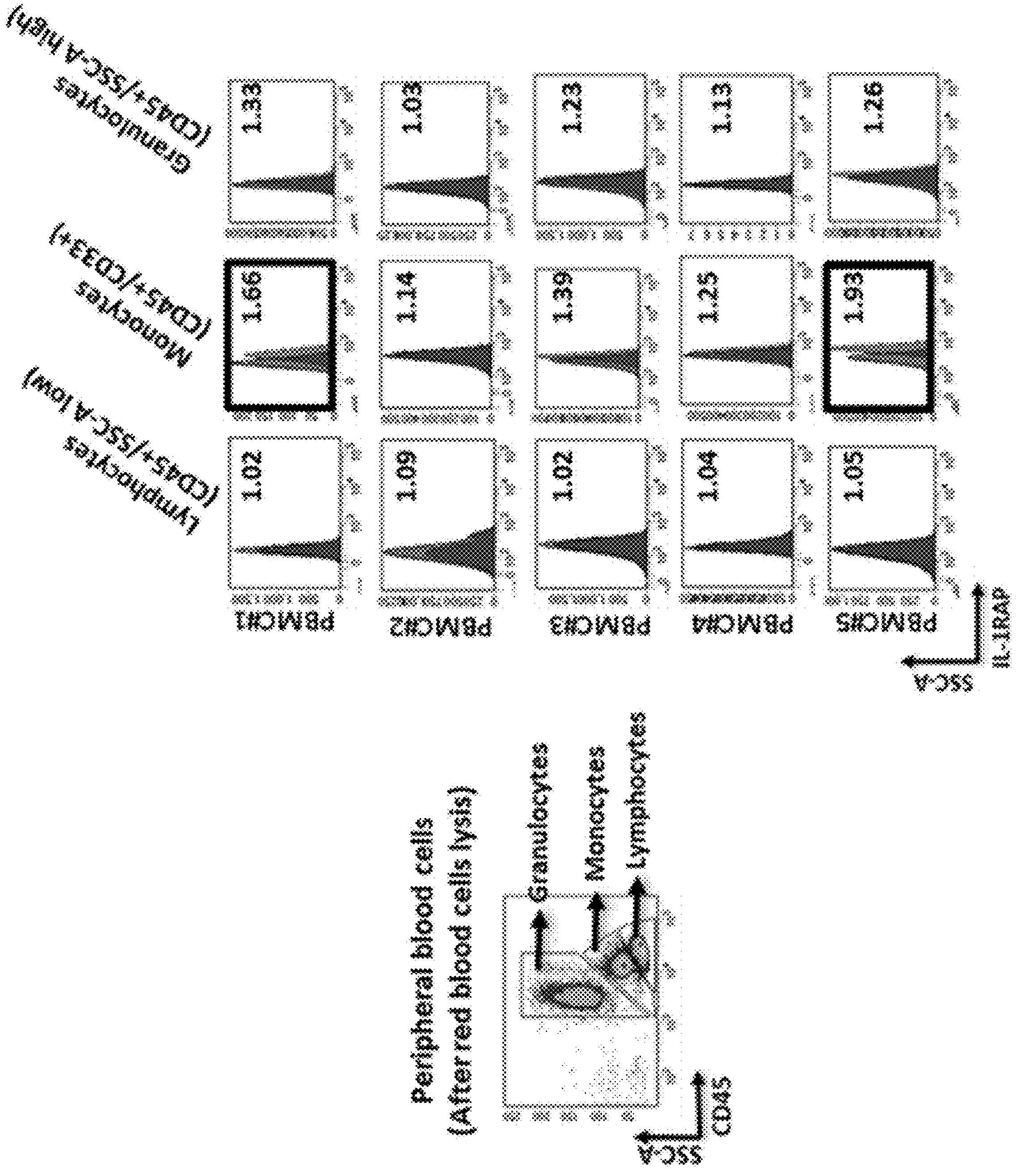
FIG. 14: Effect of IL-1RAP CAR T cells on healthy hematopoietic cells and efficiency of the safety suicide gene iCASP9 cassette. (A) IL-1RAP cell surface expression on peripheral blood (left) or bone marrow (right) cells from healthy donors (n=5). SSC-A/CD45+ allowed discrimination of subpopulations as lymphocytes (SSC-A low), monocytes (CD33+), granulocytes (SSC-A high), or HSCs (CD33−/CD34$^+$). RFI was calculated from isotype staining and provided in each window. (B) Representative (1 of 3) IL-1RAP staining of whole human cord blood cells. IL-1RAP staining is provided for whole CD34+, CD34+/CD38−, and CD34+/CD38+ HSC cord blood subpopulations. (C) IL-1RAP-positive cells among CD34+ cells in cord blood (CB, n=5) or bone marrow (BM) from healthy donors (n=5) compared to CD34+ cells from the BM (n=10) or peripheral blood (PB, n=10) from CML patients. (D) Left, Dot plot of SSC-A/CD45+ granulocyte (G), monocyte (M), and lymphocyte (L) subpopulations cultured in the presence of different effector:target (E:T) ratios of autologous non-transduced T cells or Mock or IL-1RAP CAR T cells. Right, Relative percentage of alive cells among lymphocytes (square), monocytes (circle), and granulocytes (triangle), normalized to non-transduced autologous T cells (C0) co-cultured 24 h with autologous Mock T cells (dashed line) or IL-1RAP CAR T cells (solid line). (E) Relative percentage of alive cells among the monocyte (square), KU812 (circle), or K562 (triangle) subpopulations in the presence of different E:T ratios of Mock (black, dashed line) or IL-1RAP CAR T cells (white, solid line). Percentages were calculated using absolute cell number determined using Trucount tubes based on 5000 fluorescent-bead cytometry acquisition. (F) Left, Gating strategy and analysis for absolute count of CID AP1903-induced cell death. Non-transduced (C0) or IL-1RAP CAR T cells were exposed to medium alone or medium +CID (20 nM, 24 h). The quantification was performed after acquiring 5000 fluorescent beads. Killing efficiency was normalized to control cells (untreated cells). Cell killing was calculated as follows: % Dead cells=[1−(absolute number of viable cells in AP1903-treated cells/absolute number of viable cells in untreated cells)]×100. (D) Absolute percentage of mortality. 24 h or 48 h C0 or IL-1RAP CAR (gated on CD3+/CD19+) T cell CID exposure. Right, Results are means from three independent experiments.  $p<0.001$. (G) Absolute quantification of IL-1RAP CAR T cells injected in a tumor (CML KU812, i.v.) xenograft NSG model 24 h after i.p. AP1903 (white bars) treatment (n=3 mice/group). Mice infused with control T cells (C0) were used as controls (n=2 mice/group). $p<0.01$. Number of cells is provided per ml of peripheral blood.
Figure 14B:
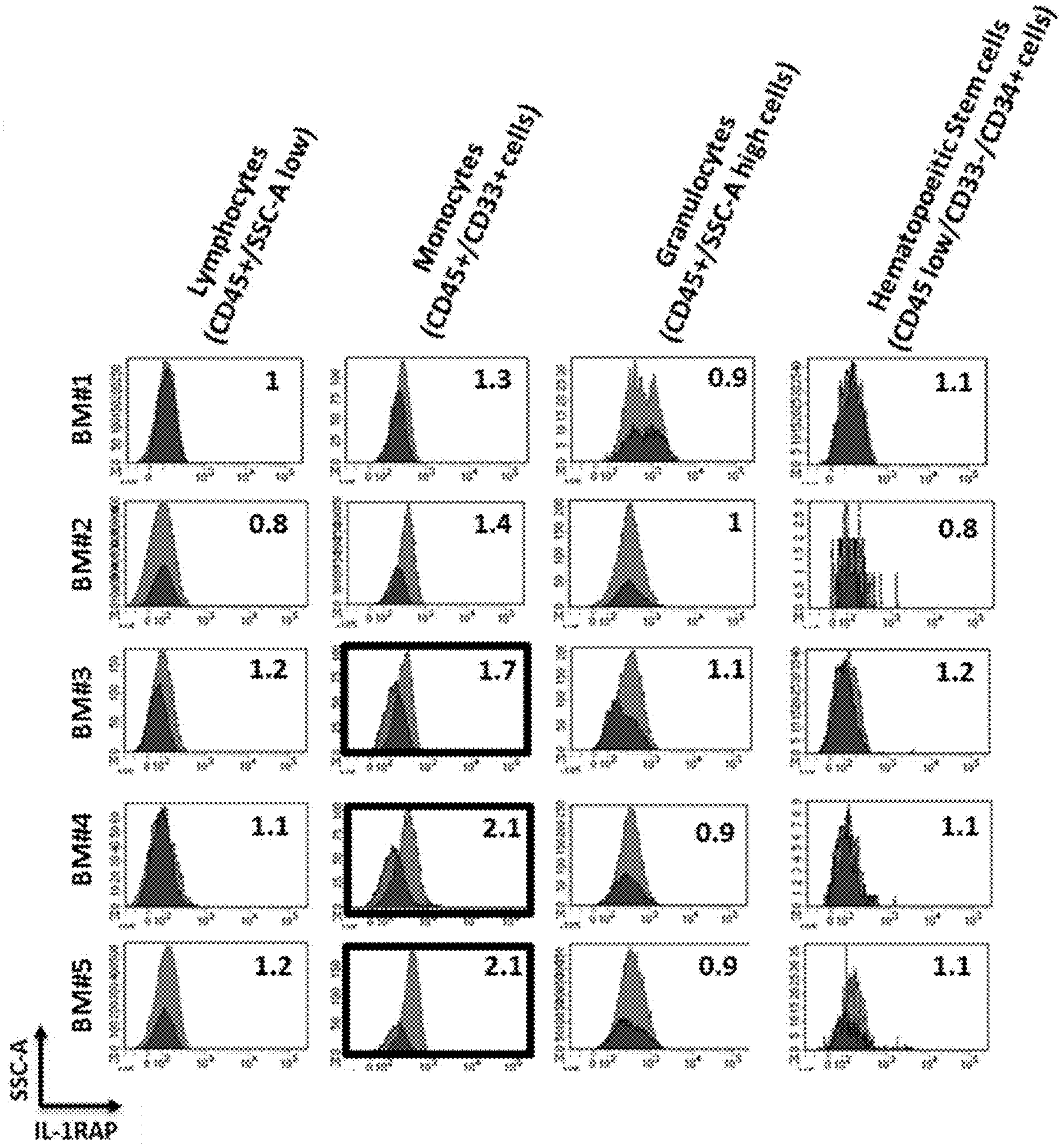
Figure 14C:
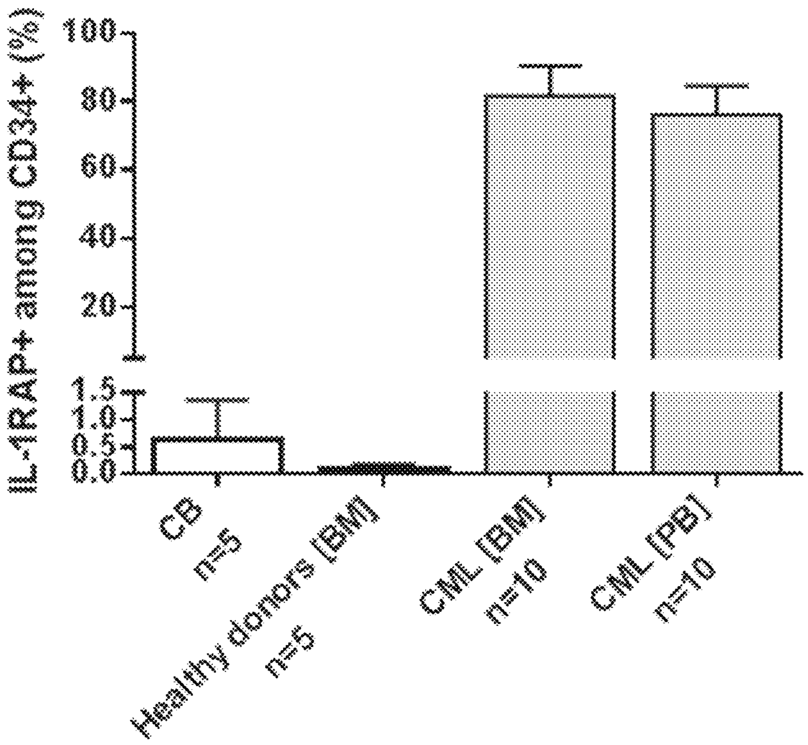
Figure 14D:
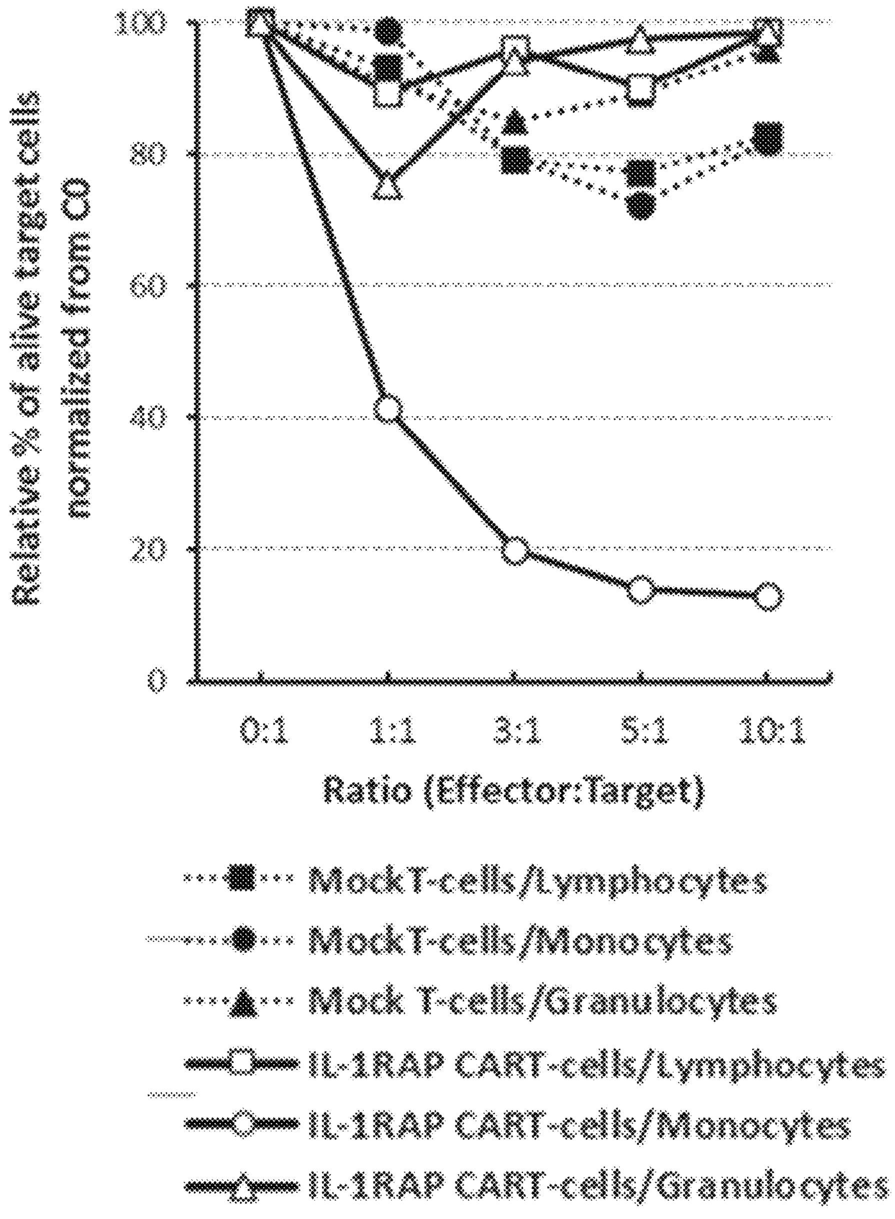
Figure 14E:
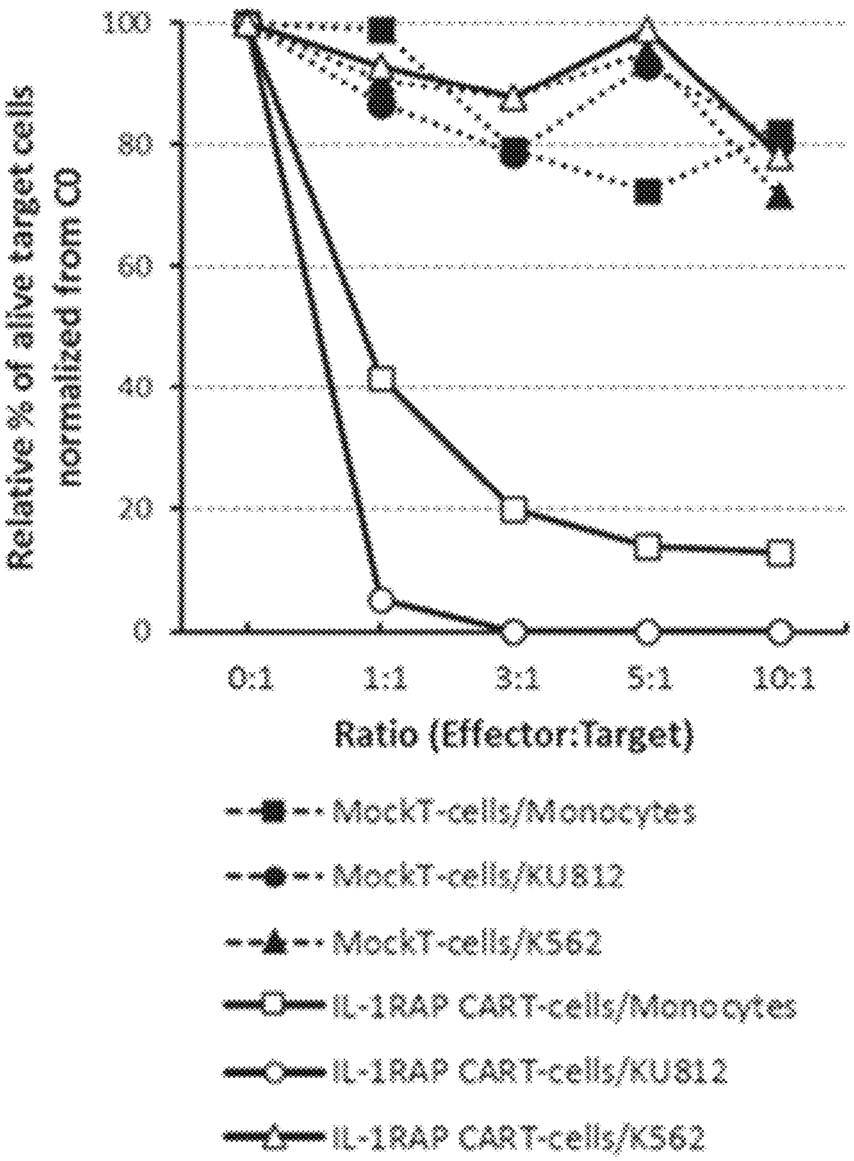

Regarding targeting of the healthy hematopoietic system, if mAb #A3C3 did not detect HSCs in bone marrow (RFI<1.2, n=5) from healthy donors (FIG. 14A, C) or normal cord blood (FIG. 14B, C), we noted weak staining (RFI<2) of the monocyte subpopulation in 2/5 peripheral blood and 3/5 bone marrow from healthy donors (FIG. 14A). Next, we studied the in vitro sensitivity of monocytes by co-culturing PBMCs and autologous CART cells at various E:T ratios. At an E:T ratio of 1:1, only some of the monocytes were targeted, leaving 41.45% of monocytes alive (FIG. 14D, right, Table 3), whereas lymphocytes, granulocytes, and the K562 IL-1RAP-negative cell line were not affected (FIG. 13D), even at superior E:T ratios. Interestingly, at this E:T ratio, 94.77% of leukemic cells were killed (FIG. 14E).

TABLE 2

IL-1RAP (mAb# A3C3) immunostaining of normal tissues

| Tissues (replicates) | Staining intensity (0 to 3+) | Comments |
|---|---|---|
| Lymph node 1 | 2+ | ~30% of endothelial cells |
| Lymph node 2 | | |
| Lymph node 3 | 1+ | ~30% of endothelial cells |
| Skeletal muscle 1 | 1+ | ~10% of endothelial cells |
| Skeletal muscle 2 | 0 | |
| Skeletal muscle 3 | 0 | |
| Prostate 1 | 1+ | ~10% of endothelial cells |
| Prostate 2 | 1+ | ~10% of endothelial cells |
| Prostate 3 | 0 | |
| Prostate 4 | 0 | |
| Prostate 5 | 0 | |
| Prostate 6 | 0 | |
| Kidney 1 | 0 | |
| Kidney 2 | 0 | |
| Kidney 3 | 0 | |
| Liver 1 | 0 | |
| Liver 2 | 0 | |
| Liver 3 | 0 | |
| Lung 1 | 2+ | |
| Lung 2 | 2+ | Few inflammatory elements |
| Lung 3 | 2+ | |
| Stomach 1 | 1+ | Few gastric mucosa cells (~10%); few epithelial cells <10% |
| Stomach 2 | 0 | |
| Stomach 3 | 0 | |
| Esophagus 1 | 0 | |
| Esophagus 2 | 0 | |
| Esophagus 3 | 0 | |
| Heart 1 | 0 | |
| Heart 2 | 0 | |
| Heart 3 | 0 | |
| Colon 1 | 3+ | |
| Colon 2 | 3+ | Epithelial cells (~30%); inflammatory elements (100%) |
| Colon 3 | 3+ | |
| Small intestine 1 | 2+ | Epithelial cells (~30%); inflammatory elements (100%) |
| Small intestine 2 | 0 | |
| Small intestine 3 | 1+ | Epithelial cells (~30%); inflammatory elements (100%) |
| Peripheral nerve 1 | 0 | |
| Peripheral nerve 2 | 0 | |
| Peripheral nerve 3 | 0 | |
| Smooth muscle 1 | 0 | |
| Smooth muscle 2 | 0 | |
| Smooth muscle 3 | 0 | |
| Cerebellum tissue 1 | 0 | |
| Cerebellum tissue 2 | 0 | |
| Cerebellum tissue 3 | 0 | |
| Ovary 1 | 0 | |
| Ovary 2 | 0 | |
| Ovary 3 | 0 | |
| Pancreas 1 | 1+ | |
| Pancreas 2 | 1+ | Cytotrophoblast cells (~10%) |
| Pancreas 3 | 1+ | |
| Salivary gland 1 | 0 | |
| Salivary gland 2 | 0 | |
| Salivary gland 3 | 0 | |
| Pituitary gland 1 | 0 | |
| Pituitary gland 2 | 0 | |
| Pituitary gland 3 | 0 | |
| Placenta 1 | 0 | |
| Placenta 2 | 0 | |
| Placenta 3 | 0 | |
| Skin 1 | 0 | |
| Skin 2 | 0 | |
| Skin 3 | 0 | |
| Spinal cord 1 | 0 | |
| Spinal cord 2 | 0 | |
| Spinal cord 3 | 0 | |
| Spleen 1 | 3+ | |
| Spleen 2 | 3+ | Necrotic elements |
| Spleen 3 | 3+ | |
| Skeletal muscle 1 | 0 | |
| Skeletal muscle 2 | 0 | |
| Skeletal muscle 3 | 0 | |
| Testis 1 | 0 | |
| Testis 2 | 0 | |
| Testis 3 | 0 | |
| Adrenal gland 1 | 0 | |
| Adrenal gland 2 | 0 | |
| Adrenal gland 3 | 0 | |
| Thyroid gland 1 | 0 | |
| Thyroid gland 2 | 0 | |
| Thyroid gland 3 | 0 | |
| Ureter 1 | 0 | |
| Ureter 2 | 0 | |
| Uterine cervix 1 | 0 | |
| Uterine cervix 2 | 0 | |
| Uterine cervix 3 | 0 | |

TABLE 3

Percentage of alive cells in different subpopulations according co-culture with different ratio of E (MockT-cells or IL-1RAP CART-cells) :T.

| E:T | Subpopulations | Mock T-cells | IL-1RAP CART-cells |
|---|---|---|---|
| [1:1] | Lymphocytes (%) | 90.79 | 75.43 |
| | Monocytes (%) | 98.71 | 41.45 |
| | Granulocytes (%) | 93.27 | 89.31 |
| [3:1] | Lymphocytes (%) | 84.98 | 94.31 |
| | Monocytes (%) | 79.19 | 19.94 |
| | Granulocytes (%) | 79.32 | 96.14 |
| [5:1] | Lymphocytes (%) | 89.1 | 97.51 |
| | Monocytes (%) | 72.31 | 13.93 |
| | Granulocytes (%) | 77.15 | 90.19 |
| [10:1] | Lymphocytes (%) | 96.13 | 98.61 |
| | Monocytes (%) | 82.03 | 13.05 |
| | Granulocytes (%) | 82.87 | 98.46 |

Figure 15:
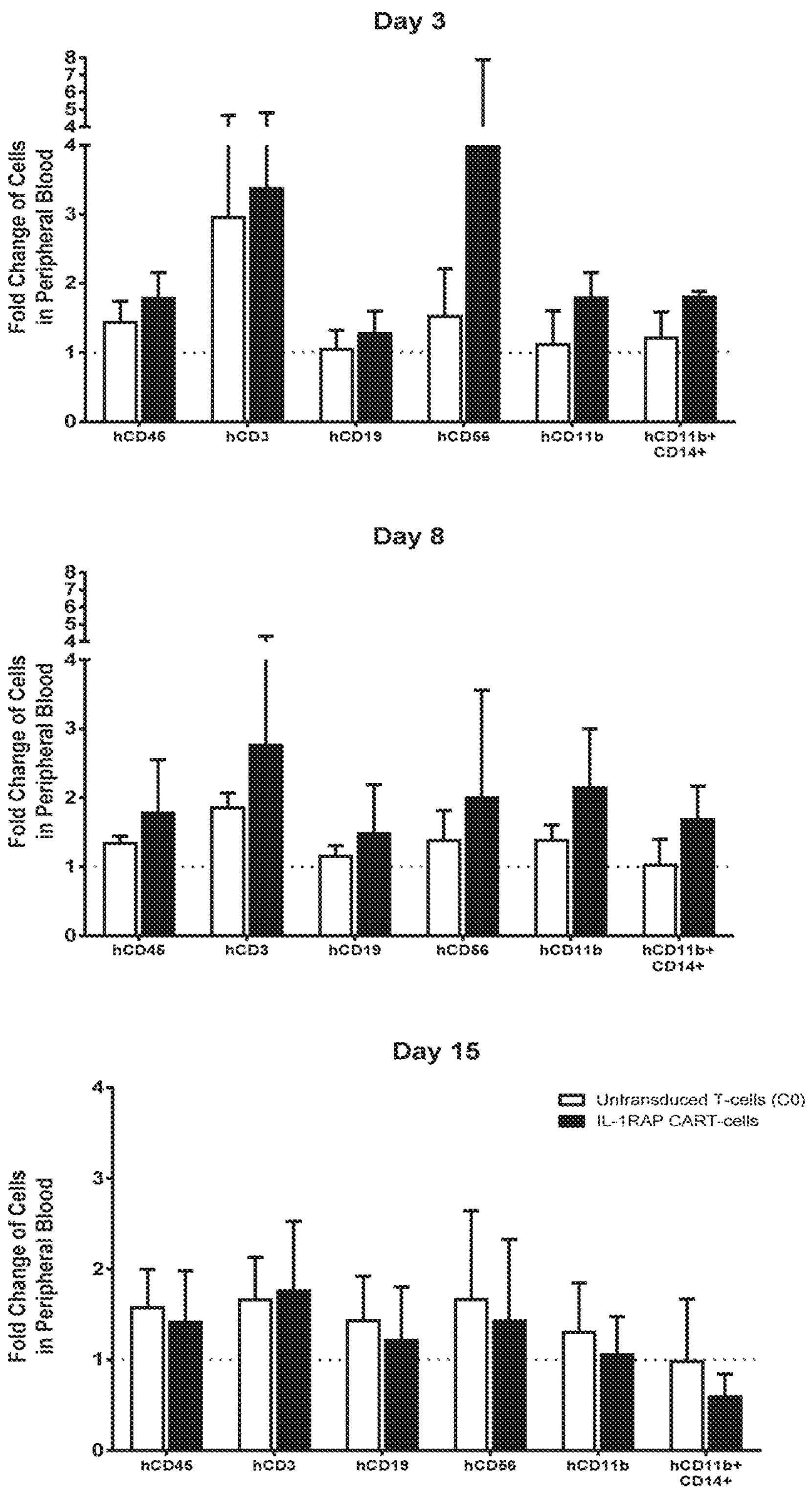
FIG. 15: Experimental human CD34+ engrafted NOG murine model in order to investigate specific toxicities of autologous IL-1RAP CART-cells against HSC and/or immune cells on a human-CD34+ cord blood cell engrafted/NOG murine model (hu-NOG). Briefly, 10.10E6 autologous CART-cells or control T-cells (C0) (produced from human CD45+ cell-sorted from murine PBMC, Spleen or Bone Marrow) were infused. Monitoring of mature immune cells (hCD3+, hCD19+, hCD56+, hCD14+, hCD11b+) was assessed at various times post infusion (Day 5, 8 and 15) by cytometry. Fold changes were calculated from immunophenotyping reference acquired at day −7 prior to CART-cells infusion. compare to time of peripheral blood harvesting (Day−9). Fold change of different immunocompetent cell subpopulations at days 3, 8 and 15 after untransduced (C0, white bars) or IL-1RAP CART-cells (black bars) compare to time of peripheral blood harvesting (Day −9). Cells count was performed from peripheral blood harvested by retro-orbital samples and Fold Change was calculated against day-7 reference. n.s: not significant.
Figure 16:
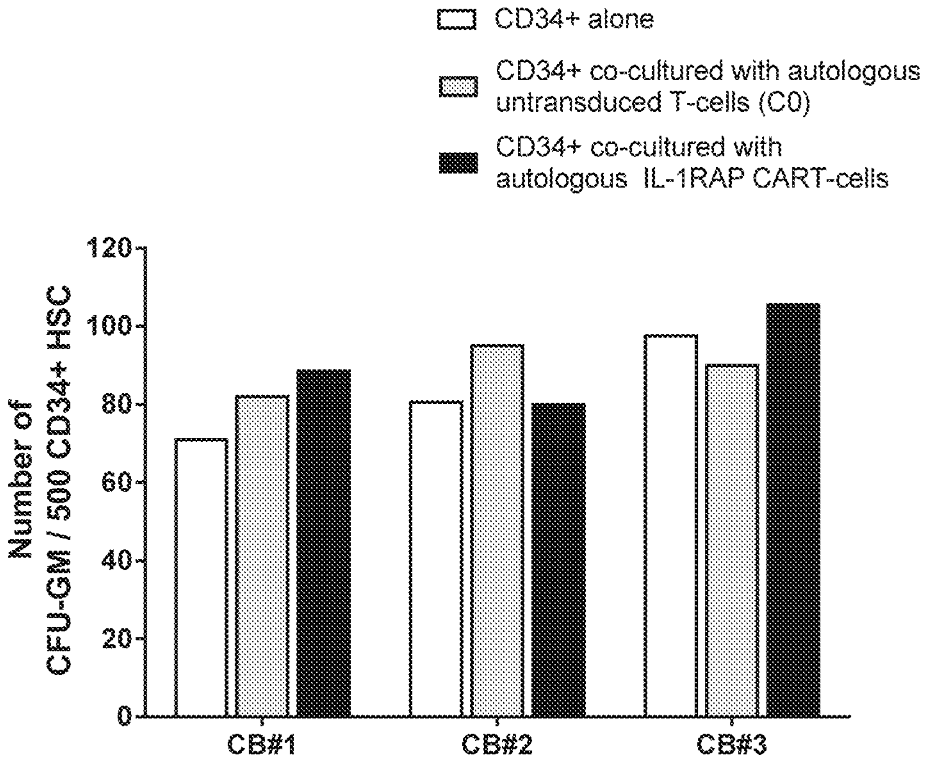
FIG. 16: Colony Forming Unit (CFU-GM) experiment from CD34+ HSC harvested from 3 different Cord Blood and cultured alone (white bars) or co-cultured with their respective autologous untransduced (C0, gray bars) or IL-1RAP CART-cells (black bars).

These results were confirmed in vivo in an hCD34-engrafted murine model (hu-NOG), in which we demonstrated that, although monocytes decreased on day 15 (41 t 25%, n=3, p=n.s), that other human immunocompetent cells derived from hCD34+ cells were not affected by CART cells (FIG. 15). Hematopoietic stem cell culture assay after in vitro co-culture of healthy CD34+ cord blood HSCs with autologous CART cells (n=3) confirmed that HSCs were not affected (FIG. 16). These results agree with IL-1RAP CART cell immunotherapy being associated with few side effects on the hematopoietic system.

Figure 14F:
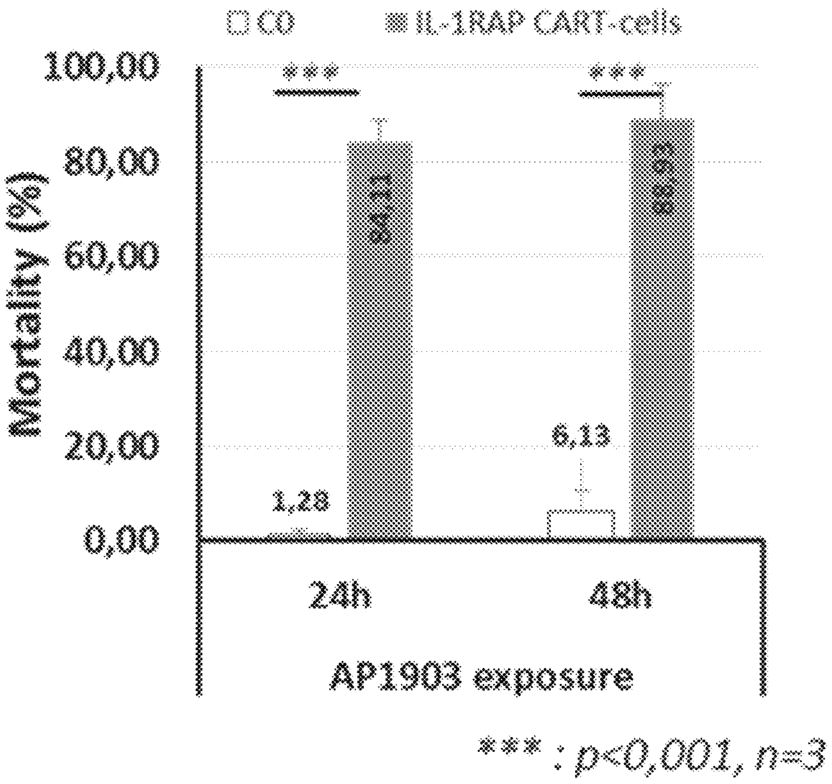
Figure 14G:
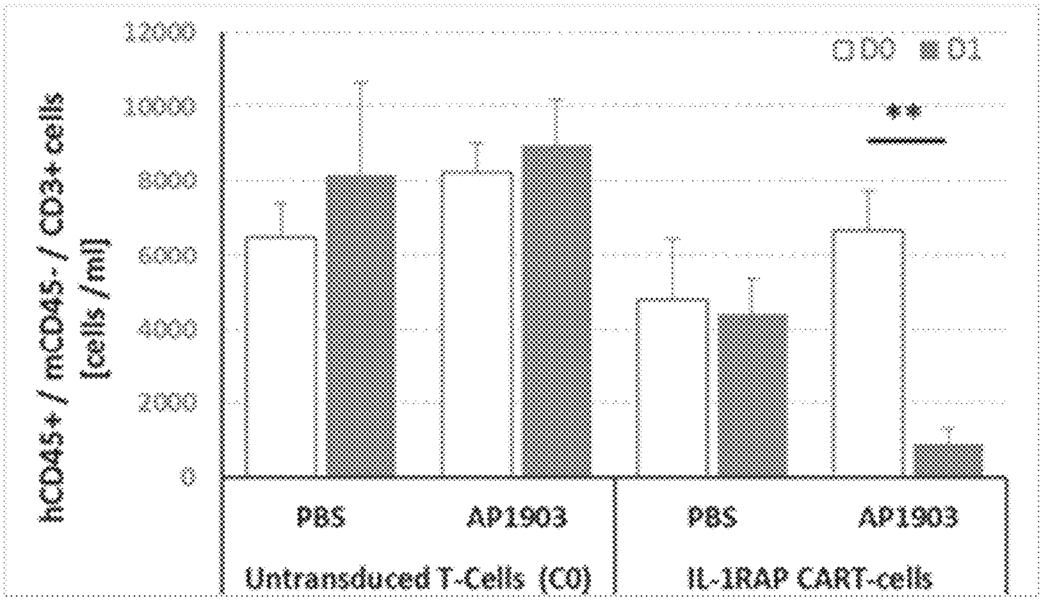
Figure 17:
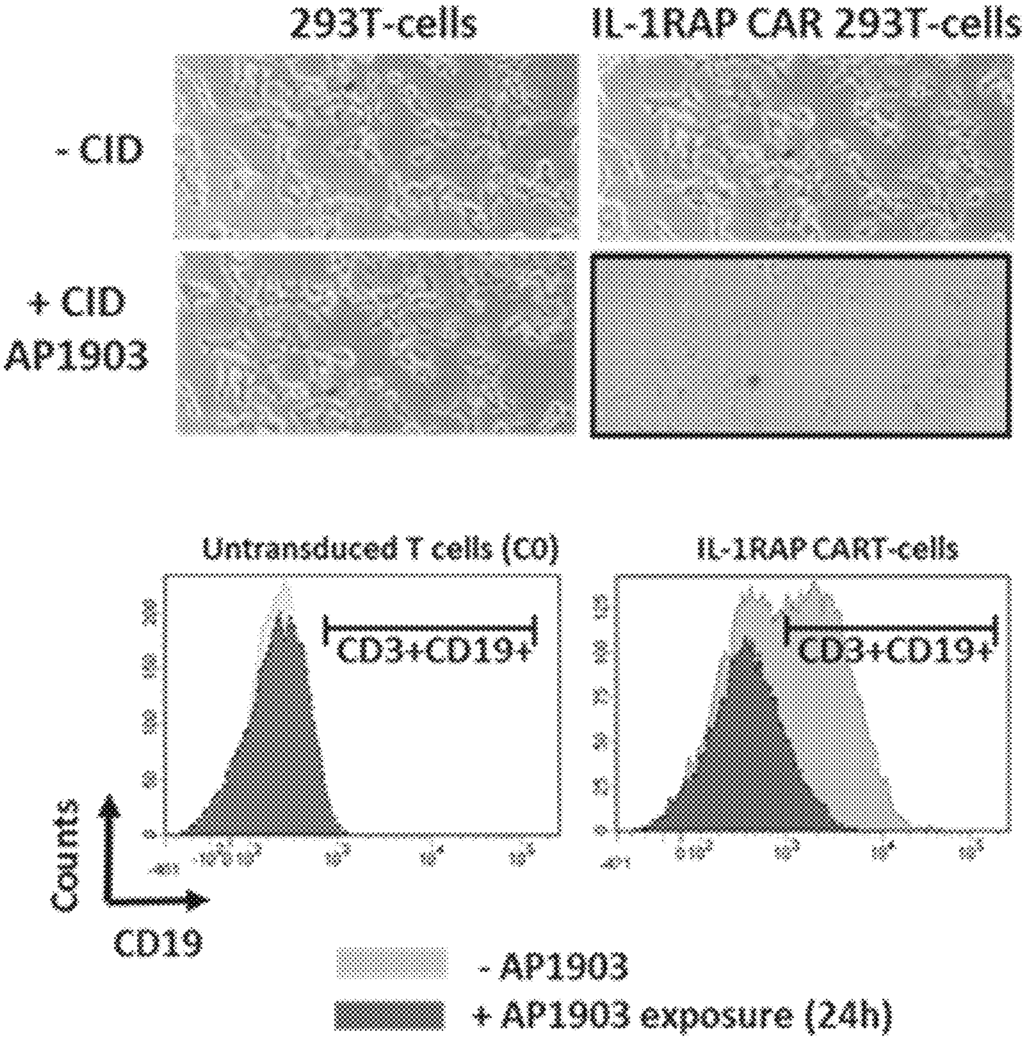
FIG. 17: Upper panel: Evaluation by optical microscopy of the CID effect on transduced 293T cells. Lower panel: Flow cytometry analysis of IL-1RAP CART cells after CID AP1930 exposure. Flow cytometry analysis after CID exposure (20 nM, 24 h, dark gray) or not (light gray) on untransduced T cells (C0) and on GMTC mixture, expressing or not IL-1RAP CAR. CD3+/CD19+ staining allowed discrimination of GMTCs expressing CAR.

In order to limit the potential toxicity, we evaluated the functionality of the safety switch of the iCASP9/AP1903 suicide system cassette after exposure to chemical inducer dimerizer (CID; 10 nM). First, using optical microscopy, we noted that 293T cell culture transduced by IL-1RAP CAR was sensitive to the CID (FIG. 17, top). Cytometric analysis showed that, in a mixed population of CD19+ and CD19− IL-1RAP CART cells, only the CD19-CD3+ cells persisted after 24 hours of CID exposure (FIG. 17, bottom). More precisely, in a quantitative assay of apoptosis, 84.11% and 88.93% of IL-1RAP CART cells were eliminated after 24 hours or 48 hours of CID exposure, respectively, compared to non-transduced T cells (C0) (1.28% and 6.13% at 24 or 48 hours, respectively; p<0.001, n=3; FIG. 14F). Finally, in vivo evaluation of the safety switch in the NSG murine model showed that 87±7.32% (p<0.01, n=3) of IL-1RAP CART cells can be eliminated after i.p. AP1903 administration but were not affected after PBS administration, whereas control untransduced T cells (C0) are not affected by either treatment (FIG. 14G).

Example 10: In Vitro Cytoxicity of IL-1RAP CART-Cells Aqainst AML Blasts from AML Patients

Materials and Methods

Untransduced T-cells (UNT-cells), MockT-cells (i.e. cells transduced with the same vector those use for CART-cells, but the vector doesn't carry the CAR) and IL-1RAP CART-cells (generated from T cells of healthy donors or AML patients) were centrifuged and resuspended in 1 ml PBS 1×, then 1 ml of an e-fluor-V450 solution diluted 1/1000 (Cell Proliferation Dye) (eBioscience) was added. The cells were incubated for 20 minutes at room temperature in the dark. Then 8 ml of complete X-Vivo® 15 medium (Lonza), 10% Fecal calf serum (GIBCO, USA), 1% of penicillin-streptomycin PS (GIBCO, USA) were added followed by an incubation for 5 minutes at +4° C. and a centrifugation at 1500 rpm for 5 minutes. The cells were washed twice with the same medium and suspended in complete X-Vivo® 15 medium, 10% human serum, 1% PBS with Interleukine 2. A co-culture of these cells with $100\times10^3$ primary cells from blood samples of AML patients (either in allogenic or in autologous settings) was carried out at different effector: target ratio (E:T ratio), in a 96-well plate (round bottom). Final volume/well=200 μl. After 24 hours of co-culture, the cytotoxicity of UNT-cells, MockT-cells and IL-1RAP CART-cells with respect to AML blasts was evaluated by viability labeling with 3 μl 7-AAD-PerCP-Cy5.5 (BD Bioscience) and a membrane staining with anti-CD34-Allophycocyanin (APC) (BD Bioscience). If necessary, the following antibodies (Abs) were used to stain, detect and discriminate AML blasts from effector cells (MockT or IL-1RAP CART-cells): 1 μl anti-CD3-phycoerythrin (PE) (Miltenyi Biotec, Germany) and 1 μl anti-CD19-Allophycocyanin (APC) (Miltenyi Biotec, Germany). Effector cells have been identified from target cells by e-fluor labeling. The results were obtained by flow cytometry and analyzed with the FACS Diva software. Allogenicity killing of IL-1RAP CART-cells is given after subtraction of cytotoxicity of control untranduced T-cells (UNT).

For the experiment where the IL-1RAP T-cells were generated from AML patients, a previous labeling of the AML blasts was performed after isolation of T-cells in order to check the presence or not of T and B-cells.

Results

Figure 19A:
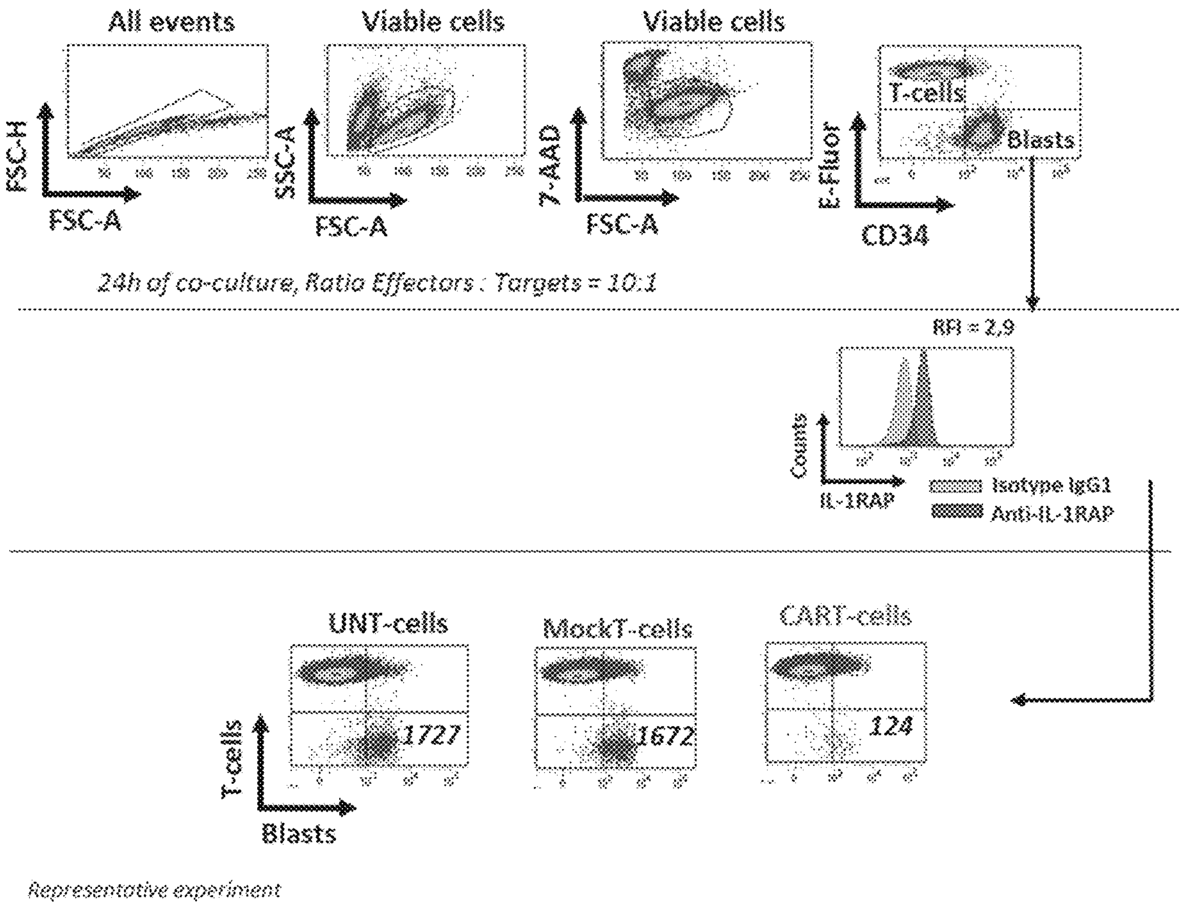
FIG. 19: AML blasts cytotoxicity of IL-1RAP CART-Cells. The gating strategy is represented. The CD34 antibody was used to identify target AML blasts (FIG. 19A). The number of events of AML blasts showing the cytotoxicity of IL-1RAP CART-cells is also shown (FIG. 19A). The results of three independent experiments are shown on FIG. 19B. Legend of FIGS. 19A and 19B: FSC: Forward Scatter, indicates the size of the cells. 7-AAD: 7-aminoactinimycin D, a cell viability marker. E-Fluor: a dye that stain the cell membrane. #1 and #2 experiments were performed with allogenic IL-1RAP CART-cells produced from healthy donors. #3 experiment was performed with allogenic IL-1RAP CART-cells produced from T-cells of an AML patient. Living cells means living AML blasts.
Figure 19B:
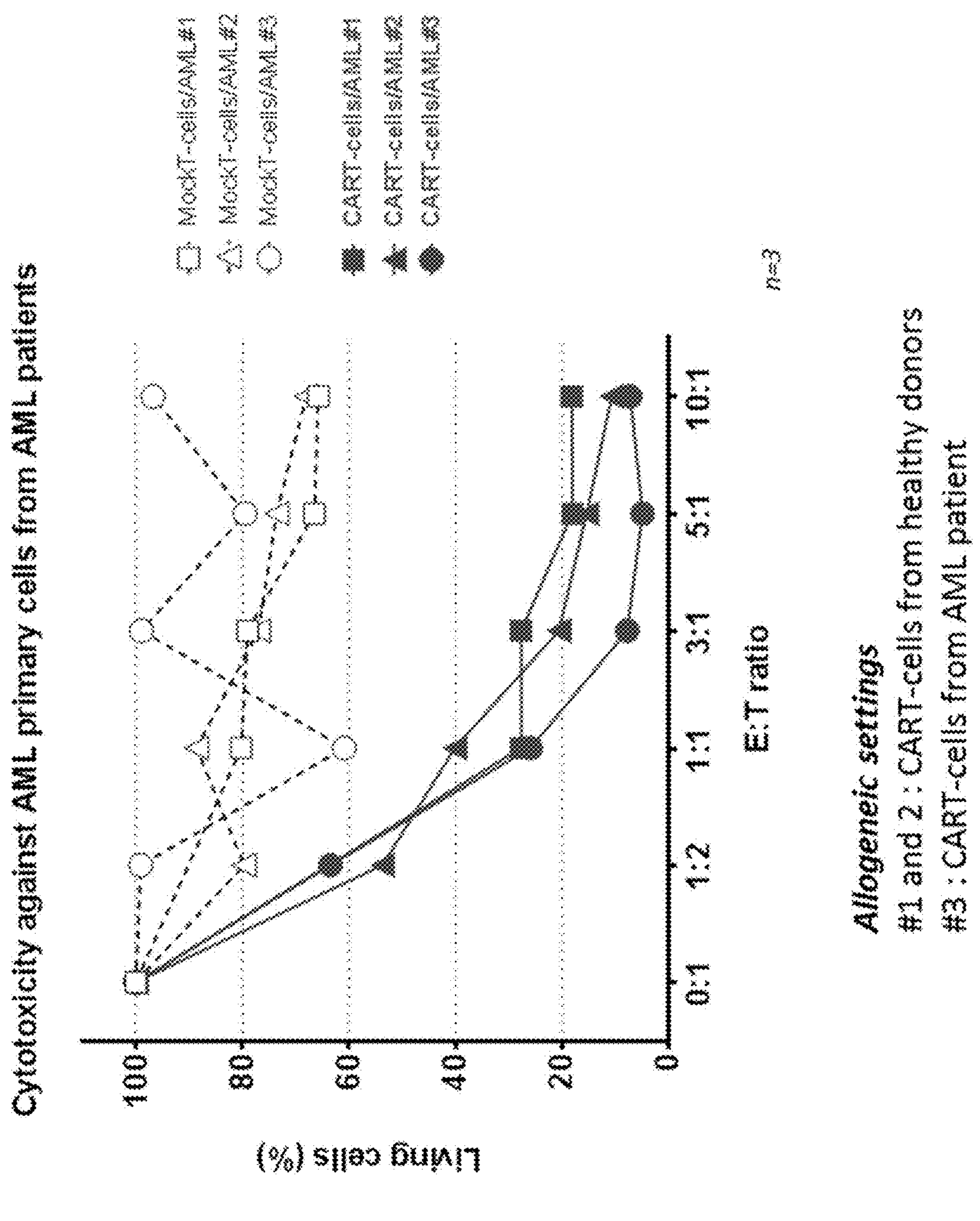
Figure 20A:
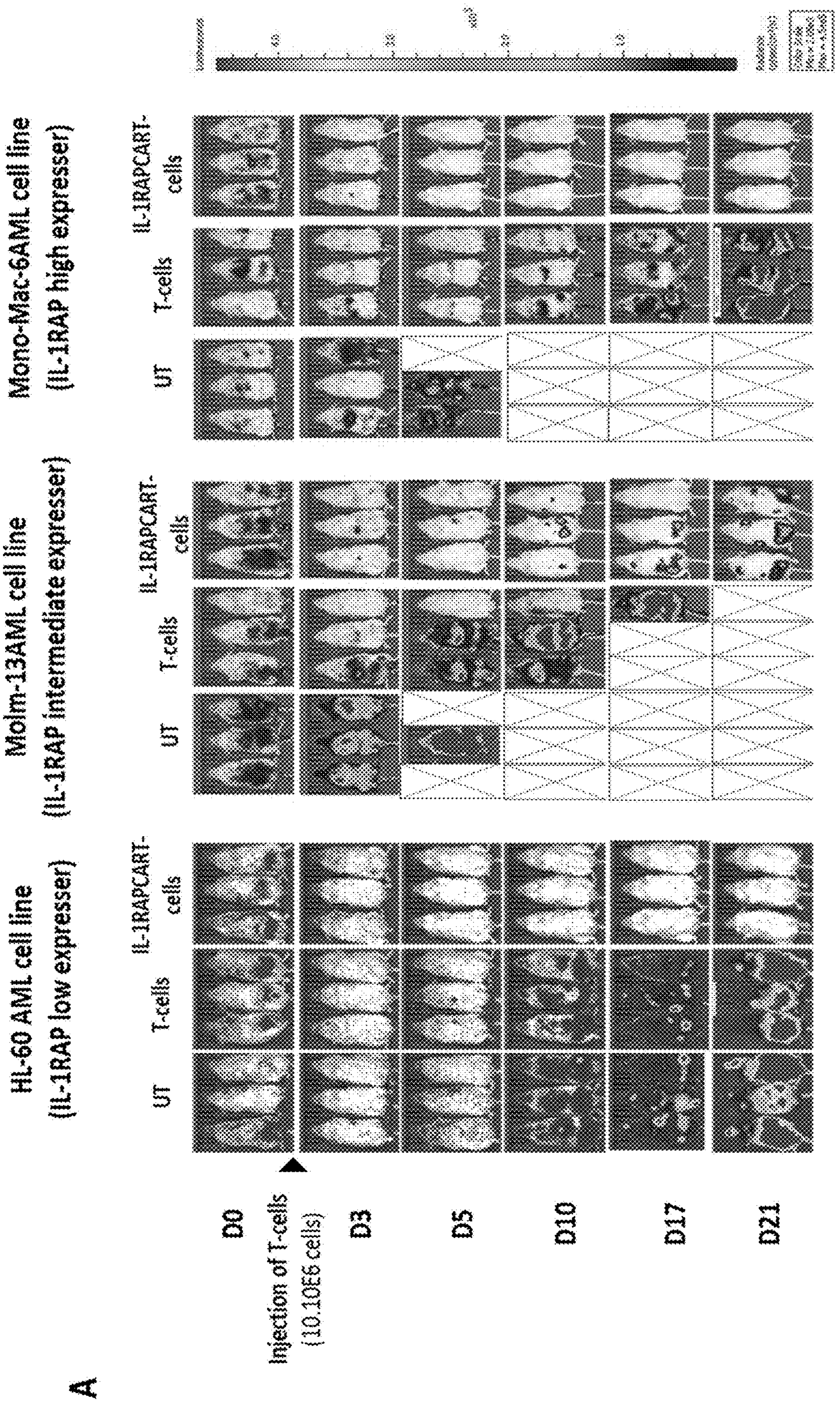
FIG. 20A: on day 0, following AML cell injection, mice were untreated or treated with control T-cells, i.e. MockT or UNT cells ($10\times10^6$ cells in 300 μL of PBS), or IL-1RAP CAR-T cells ($10\times10^6$ cells in 300 μL of PBS) and monitored on days as mentioned using bioluminescence imaging (BLI) for leukemia development. Bioluminescent imaging analysis of mice was performed for the different groups from days 0 to 21. Legend: (x): dead mice. ▲: UNT or IL-1RAP CAR T-cells injection.
Figure 20B:
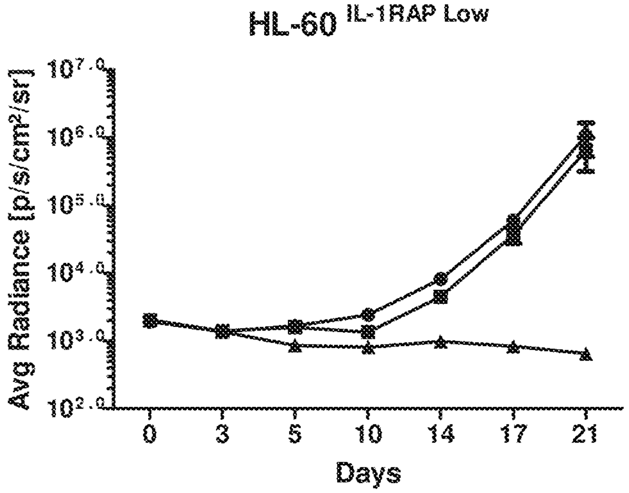
FIG. 20B: Radiance of the in vivo bioluminescent signal (radiance p/s/cm2/sr) harvested using bioluminescence imaging (BLI).
Figure 20B:
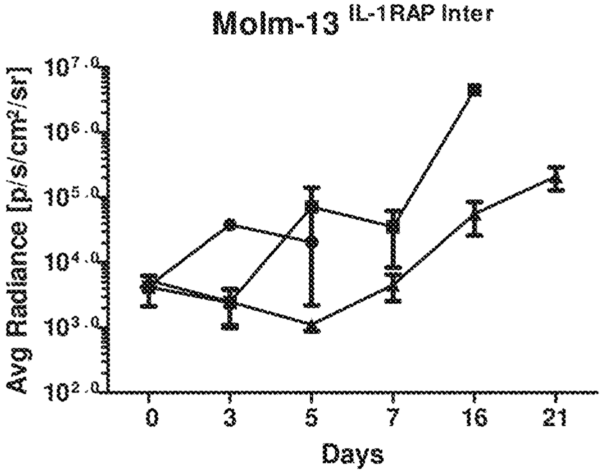
Figure 20B:
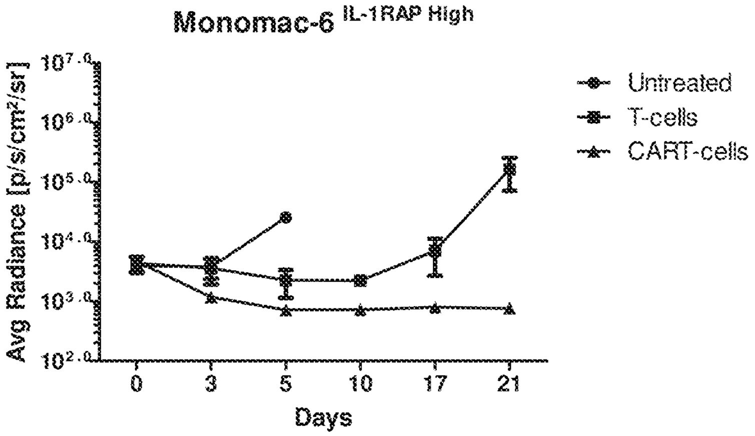

The results are presented in FIG. 19. Compared to MOCKT-cells or UNT-cells, where no cytotoxicity was detected, co-culture with IL-1RAP CART-cells at various E:T ratio allowed to kill AML blasts (Low and intermediate IL-1RAP expressers, previously identified by flow cytometry (not shown)) primary cells from AML patients with the same efficiency regardless level of tumor antigen expression.

Interestingly, IL-1RAP CART-cells generated from T-cells of AML patient were also able to kill AML blasts with the same efficiency. It confirms that CART-cells can be generated from AML patients and used in autologous settings.

Example 11: In Vivo Cytoxicity of IL-1RAP CART-Cells Against AML Blasts from AML Patients

Materials and Methods

HL-60, Molm-13 and Mono-Mac-6 AML, respectively low, intermediate (int) and High IL-1RAP expressing cell lines were transduced with Luciferase lentiviral vector (pLenti CMV V5-Luc Blast vector, Addgene). Luciferase positive cells were selected by resistance to blasticidin (ThermoFisher Scientific).

Six- to 8-week-old NSG mice (Jackson Laboratory, Sacramento, CA, USA) were sublethally irradiated (25 Gy) on day 4. On day 3, each mouse was injected via tail vein, with $1\times10^6$ of HL-60 or Molm-13 or Mono-Mac-6 luciferase-expressing AML cells suspended in 300 μL of PBS. On day 0, following AML cell injection, mice were untreated (UT) or treated with untransduced T cells (UNT) ($10\times10^6$ cells in 300 μL of PBS), or IL-1RAP CAR-T cells ($10\times10^6$ cells in 300 μL of PBS) via tail vein and monitored at days 3, 5, 10, 14, 17 and 21 using the IVIS® lumina III system (PerkinElmer) for leukemia development.

Animal protocols were performed under control of the animal care and use committee of the University of Besangon. Mice were followed until the animals in the untreated group reached a moribund health state and signs of leukemia manifested (i.e. weight loss >15%, decreased activity, and/or hindlimb paralysis). Mouse experimentations were approved by the local ethical committees (CELEAG and protocol 11007R, Veterinary Services for Animal Health & Protection, respectively for NSG-S models).

Results

The results are presented in FIG. 20. It has been shown, compared to untreated or UNT treated T cells mice groups, that IL-1RAP CART-cells significantly reduce leukemia burden in the AML in vivo xenograft mouse models independently of the IL-1RAP cell surface expression of leukemic cells.

The invention claimed is:

1. A method for treating acute myeloid leukemia (AML), wherein the AML is IL-1RAP-expressing AML, the method comprising administering a cell expressing a nucleic acid molecule encoding a chimeric antigen receptor (CAR) at its membrane, wherein the CAR comprises an antibody or antibody fragment which includes an anti-IL-1RAP binding domain, a transmembrane domain, and an intracellular signaling domain comprising at least a stimulatory domain, and wherein said anti-IL-1RAP binding domain comprises:

(i) a light chain comprising a complementarity determining region 1 (CDR1) comprising the amino acid sequence SEQ ID NO: 6, a complementarity determining region 2 (CDR2) comprising the amino acid sequence SEQ ID NO: 7 and a complementarity determining region 3 (CDR3) comprising the amino acid sequence SEQ ID NO: 8, and (ii) a heavy chain comprising a complementarity determining region 1 (CDR1) comprising the amino acid sequence SEQ ID NO: 12, a complementarity determining region 2 (CDR2) comprising the amino acid sequence SEQ ID NO: 13 and a complementarity determining region 3 (CDR3) comprising the amino acid sequence SEQ ID NO: 14.

2. The method according to claim 1, wherein the cell is a T cell.

3. The method according to claim 1, wherein the IL-1RAP binding domain is selected from the group consisting of an antibody, a Fv, a scFv, a Fab, or another antibody fragment.

4. The method according to claim 1, wherein said transmembrane domain is a transmembrane domain of a protein selected from the group consisting of the alpha, beta or zeta chain of the T-cell receptor, CD28, CD3 epsilon, CD45, CD4, CD5, CD8, CD9, CD 16, CD22, CD33, CD37, CD64, CD80, CD86, CD134, CD137 and CD154.

5. The method according to claim 1, wherein the anti-IL-1RAP binding domain is connected to the transmembrane domain by a hinge region.

6. The method according to claim 1, wherein the intracellular signaling domain comprises at least one costimulatory domain.

7. The method according to claim 1, wherein the AML is (i) refractory/relapsed AML or (ii) AML with complex cytogenetic abnormalities and/or AML with TP53 mutations.

8. The method according to claim 1, wherein the cell is administered with at least one monoclonal antibody.

9. The method according to claim 1, wherein the method is an autologous treatment.

10. The method according to claim 2, wherein the T cell is a CD8+ T cell.

11. The method according to claim 3, wherein the IL-1RAP binding domain is a scFv.

12. The method according to claim 4, wherein the transmembrane domain is a transmembrane domain of CD28.

13. The method according to claim 5, wherein the hinge region comprises a hinge sequence of IgG1 or a sequence with 95-99% identity thereto.

14. The method according to claim 6, wherein the at least one costimulatory domain is a functional intracellular signaling domain obtained from one or more proteins selected from the group consisting of OX40, CD2, CD27, CD28, CDS, CD3 zeta, ICAM-1, LFA-1, ICOS, and 4-1BB.

15. The method according to claim 1, wherein the AML is a refractory/relapsed IL-1RAP expressing AML.

16. The method according to claim 8, wherein the cell is administered with at least one anti-checkpoint inhibitor.

* * * * *

SEQUENCE LISTING

```
<160> NUMBER OF SEQ ID NOS: 18

<210> SEQ ID NO 1
<211> LENGTH: 423
<212> TYPE: DNA
<213> ORGANISM: Artificial Sequence
<220> FEATURE:
<223> OTHER INFORMATION: Nucleotide sequence coding chain H (VH) of
      murine scFv anti-IL-1RAP

<400> SEQUENCE: 1

atgggatgga gctgtatcat cctcttcttg gtagcaacag ctacaggtgt caactcccag     60

gtccaactgc agcagcctgg ggctgagctt atgatgcctg gggcttcagt gaaagtgtcc    120

tgcgaggctt ctggctacac attcactgac tcctggatgc actgggtgaa gcagaggcct    180

ggacaaggcc ttgagtggat cggagcgatt gatccttctg atagttatac tacctataat    240

caaaaattca cgggcaaggc cacattgagt gtagacgaat cctccaacac agcctacatg    300

cagctcagca gcctgacatc tgaggactct gcggtctatt actgtgcaag gtattactcc    360

ggtagtaact acatatcgcc ctttccttac tggggccaag ggactctggt cactgtctct    420

gca                                                                  423


<210> SEQ ID NO 2
<211> LENGTH: 141
<212> TYPE: PRT
<213> ORGANISM: Artificial Sequence
<220> FEATURE:
<223> OTHER INFORMATION: Amino acid sequence of chain H (VH) of murine
      scFv anti-IL-1RAP

<400> SEQUENCE: 2

Met Gly Trp Ser Cys Ile Ile Leu Phe Leu Val Ala Thr Ala Thr Gly
1               5                   10                  15

Val Asn Ser Gln Val Gln Leu Gln Gln Pro Gly Ala Glu Leu Met Met
            20                  25                  30

Pro Gly Ala Ser Val Lys Val Ser Cys Glu Ala Ser Gly Tyr Thr Phe
        35                  40                  45

Thr Asp Ser Trp Met His Trp Val Lys Gln Arg Pro Gly Gln Gly Leu
    50                  55                  60

Glu Trp Ile Gly Ala Ile Asp Pro Ser Asp Ser Tyr Thr Thr Tyr Asn
65                  70                  75                  80

Gln Lys Phe Thr Gly Lys Ala Thr Leu Ser Val Asp Glu Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Ser Gly Ser Asn Tyr Ile Ser Pro Phe
        115                 120                 125

Pro Tyr Trp Gly Gln Gly Thr Leu Val Thr Val Ser Ala
```

-continued 130 135 140

<210> SEQ ID NO 3
<211> LENGTH: 382
<212> TYPE: DNA
<213> ORGANISM: Artificial Sequence
<220> FEATURE:
<223> OTHER INFORMATION: Nucleotide sequence coding chain K (VL) of murine scFv anti-IL-1RAP

<400> SEQUENCE: 3
atggagtcac agattcaggt ctttgtattc gtgtttctct ggttgtctgg tgttgacgga 60
gacattgtga tgacccagtc tcacaaattc atgtccacat cagtaggaga cagggtcacc 120
atcacctgca aggccagtct ggatgtgagt actgctgtgg cctggtatca acagaaacca 180
ggacaatctc ctaaactact gatttactcg gcatcctacc ggtacactgg agtccctgat 240
cgcttcactg gcagtggatc tgggacggat ttcactttca ccatcagcag tgtgcaggct 300
gaagacctgg cagtttatta ctgtcagcaa cattatagtc ctccattcac gttcggctcg 360
gggacaaact tggagataaa ac 382

<210> SEQ ID NO 4
<211> LENGTH: 127
<212> TYPE: PRT
<213> ORGANISM: Artificial Sequence
<220> FEATURE:
<223> OTHER INFORMATION: Amino acid sequence of chain K (VL) of murine scFv anti-IL-1RAP

<400> SEQUENCE: 4

Met Glu Ser Gln Ile Gln Val Phe Val Phe Val Phe Leu Trp Leu Ser
1 5 10 15

Gly Val Asp Gly Asp Ile Val Met Thr Gln Ser His Lys Phe Met Ser
20 25 30

Thr Ser Val Gly Asp Arg Val Thr Ile Thr Cys Lys Ala Ser Leu Asp
35 40 45

Val Ser Thr Ala Val Ala Trp Tyr Gln Gln Lys Pro Gly Gln Ser Pro
50 55 60

Lys Leu Leu Ile Tyr Ser Ala Ser Tyr Arg Tyr Thr Gly Val Pro Asp
65 70 75 80

Arg Phe Thr Gly Ser Gly Ser Gly Thr Asp Phe Thr Phe Thr Ile Ser
85 90 95

Ser Val Gln Ala Glu Asp Leu Ala Val Tyr Tyr Cys Gln Gln His Tyr
100 105 110

Ser Pro Pro Phe Thr Phe Gly Ser Gly Thr Asn Leu Glu Ile Lys
115 120 125

<210> SEQ ID NO 5
<211> LENGTH: 15
<212> TYPE: PRT
<213> ORGANISM: Artificial Sequence
<220> FEATURE:
<223> OTHER INFORMATION: Linker between the VH and VL domains

<400> SEQUENCE: 5

Gly Gly Ser Gly Gly Gly Gly Ser Gly Gly Gly Gly Ser Val Asp
1 5 10 15

<210> SEQ ID NO 6
<211> LENGTH: 6
<212> TYPE: PRT

<213> ORGANISM: Artificial Sequence
<220> FEATURE:
<223> OTHER INFORMATION: CDR1 of the light chain

<400> SEQUENCE: 6

Leu Asp Val Ser Thr Ala
1 5

<210> SEQ ID NO 7
<211> LENGTH: 3
<212> TYPE: PRT
<213> ORGANISM: Artificial Sequence
<220> FEATURE:
<223> OTHER INFORMATION: CDR2 of the light chain

<400> SEQUENCE: 7

Ser Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: CDR3 of the light chain

<400> SEQUENCE: 8

Gln Gln His Tyr Ser Pro Pro Phe Thr
1 5

<210> SEQ ID NO 9
<211> LENGTH: 18
<212> TYPE: DNA
<213> ORGANISM: Artificial Sequence
<220> FEATURE:
<223> OTHER INFORMATION: CDR1 of the light chain (nt)

<400> SEQUENCE: 9
ctggatgtga gtactgct 18

<210> SEQ ID NO 10
<211> LENGTH: 9
<212> TYPE: DNA
<213> ORGANISM: Artificial Sequence
<220> FEATURE:
<223> OTHER INFORMATION: CDR2 of the light chain (nt)

<400> SEQUENCE: 10 tcggcatcc 9

<210> SEQ ID NO 11
<211> LENGTH: 27
<212> TYPE: DNA
<213> ORGANISM: Artificial Sequence
<220> FEATURE:
<223> OTHER INFORMATION: CDR3 of the light chain (nt)

<400> SEQUENCE: 11
cagcaacatt atagtcctcc attcacg 27

<210> SEQ ID NO 12
<211> LENGTH: 8
<212> TYPE: PRT
<213> ORGANISM: Artificial Sequence
<220> FEATURE:
<223> OTHER INFORMATION: CDR1 of the heavy chain

<400> SEQUENCE: 12

Gly Tyr Thr Phe Thr Asp Ser Trp
1 5

<210> SEQ ID NO 13
<211> LENGTH: 8
<212> TYPE: PRT
<213> ORGANISM: Artificial Sequence
<220> FEATURE:
<223> OTHER INFORMATION: CDR2 of the heavy chain

<400> SEQUENCE: 13

Ile Asp Pro Ser Asp Ser Tyr Thr
1 5

<210> SEQ ID NO 14
<211> LENGTH: 15
<212> TYPE: PRT
<213> ORGANISM: Artificial Sequence
<220> FEATURE:
<223> OTHER INFORMATION: CDR3 of the heavy chain

<400> SEQUENCE: 14

Ala Arg Tyr Tyr Ser Gly Ser Asn Tyr Ile Ser Pro Phe Pro Tyr
1 5 10 15

<210> SEQ ID NO 15
<211> LENGTH: 24
<212> TYPE: DNA
<213> ORGANISM: Artificial Sequence
<220> FEATURE:
<223> OTHER INFORMATION: CDR1 of the heavy chain (nt)

<400> SEQUENCE: 15
ggctacacat tcactgactc ctgg 24

<210> SEQ ID NO 16
<211> LENGTH: 24
<212> TYPE: DNA
<213> ORGANISM: Artificial Sequence
<220> FEATURE:
<223> OTHER INFORMATION: CDR2 of the heavy chain (nt)

<400> SEQUENCE: 16
attgatcctt ctgatagtta tact 24

<210> SEQ ID NO 17
<211> LENGTH: 45
<212> TYPE: DNA
<213> ORGANISM: Artificial Sequence
<220> FEATURE:
<223> OTHER INFORMATION: CDR3 of the heavy chain (nt)

<400> SEQUENCE: 17
gcaaggtatt actccggtag taactacata tcgccctttc cttac 45

<210> SEQ ID NO 18
<211> LENGTH: 283
<212> TYPE: PRT
<213> ORGANISM: Artificial Sequence
<220> FEATURE:
<223> OTHER INFORMATION: Amino acid sequence of murine scFv anti-IL-1RAP (i.e. #A3C3 CAR)

<400> SEQUENCE: 18

Met Gly Trp Ser Cys Ile Ile Leu Phe Leu Val Ala Thr Ala Thr Gly

-continued

```
1               5                   10                  15

Val Asn Ser Gln Val Gln Leu Gln Gln Pro Gly Ala Glu Leu Met Met
            20                  25                  30

Pro Gly Ala Ser Val Lys Val Ser Cys Glu Ala Ser Gly Tyr Thr Phe
        35                  40                  45

Thr Asp Ser Trp Met His Trp Val Lys Gln Arg Pro Gly Gln Gly Leu
    50                  55                  60

Glu Trp Ile Gly Ala Ile Asp Pro Ser Asp Ser Tyr Thr Thr Tyr Asn
65                  70                  75                  80

Gln Lys Phe Thr Gly Lys Ala Thr Leu Ser Val Asp Glu Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Ser Gly Ser Asn Tyr Ile Ser Pro Phe
        115                 120                 125

Pro Tyr Trp Gly Gln Gly Thr Leu Val Thr Val Ser Ala Gly Gly Ser
    130                 135                 140

Gly Gly Gly Gly Ser Gly Gly Gly Gly Ser Val Asp Met Glu Ser Gln
145                 150                 155                 160

Ile Gln Val Phe Val Phe Val Phe Leu Trp Leu Ser Gly Val Asp Gly
                165                 170                 175

Asp Ile Val Met Thr Gln Ser His Lys Phe Met Ser Thr Ser Val Gly
            180                 185                 190

Asp Arg Val Thr Ile Thr Cys Lys Ala Ser Leu Asp Val Ser Thr Ala
        195                 200                 205

Val Ala Trp Tyr Gln Gln Lys Pro Gly Gln Ser Pro Lys Leu Leu Ile
    210                 215                 220

Tyr Ser Ala Ser Tyr Arg Tyr Thr Gly Val Pro Asp Arg Phe Thr Gly
225                 230                 235                 240

Ser Gly Ser Gly Thr Asp Phe Thr Phe Thr Ile Ser Ser Val Gln Ala
                245                 250                 255

Glu Asp Leu Ala Val Tyr Tyr Cys Gln Gln His Tyr Ser Pro Pro Phe
            260                 265                 270

Thr Phe Gly Ser Gly Thr Asn Leu Glu Ile Lys
        275                 280
```